(12) United States Patent
Appleyard et al.

(10) Patent No.: US 9,192,569 B2
(45) Date of Patent: Nov. 24, 2015

(54) FORMULATIONS FOR INFUSION OF TYPE B LANTIBIOTICS

(75) Inventors: Antony Nicholas Appleyard, Hertfordshire (GB); Sjoerd Nicolaas Wadman, Hertfordshire (GB)

(73) Assignee: Novacta Biosystems Limited, Hertfordshire (GB)

( * ) Notice: Subject to any disclaimer, the term of this patent is extended or adjusted under 35 U.S.C. 154(b) by 30 days.

(21) Appl. No.: 13/816,063

(22) PCT Filed: Aug. 9, 2011

(86) PCT No.: PCT/GB2011/001191
§ 371 (c)(1),
(2), (4) Date: Feb. 8, 2013

(87) PCT Pub. No.: WO2012/020219
PCT Pub. Date: Feb. 16, 2012

(65) Prior Publication Data
US 2013/0137630 A1    May 30, 2013

(30) Foreign Application Priority Data
Aug. 11, 2010 (GB) .................................. 1013513.5

(51) Int. Cl.
| | |
|---|---|
| A61K 9/19 | (2006.01) |
| A61K 38/10 | (2006.01) |
| A61K 47/26 | (2006.01) |
| A61K 9/00 | (2006.01) |
| A61K 38/16 | (2006.01) |

(52) U.S. Cl.
CPC ................ *A61K 9/0019* (2013.01); *A61K 9/19* (2013.01); *A61K 38/164* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 3,710,795 A | 1/1973 | Higuchi et al. | |
| 5,112,806 A | 5/1992 | Chatterjee et al. | |
| 5,304,540 A | 4/1994 | Blackburn et al. | |
| 5,667,991 A | 9/1997 | Koller et al. | |
| 5,683,675 A | 11/1997 | Vedia et al. | |
| 5,763,395 A | 6/1998 | Blackburn et al. | |
| 5,958,873 A | 9/1999 | Sakr et al. | |
| 5,985,823 A | 11/1999 | Goldstein | |
| 6,022,851 A | 2/2000 | Vertesy et al. | |
| 6,569,830 B1 | 5/2003 | Climo et al. | |
| 7,056,942 B2 | 6/2006 | Hildesheim et al. | |
| 7,122,514 B2 | 10/2006 | Climo et al. | |
| 7,989,416 B2 | 8/2011 | Boakes et al. | |
| 8,283,371 B2 | 10/2012 | Wadman | |
| 8,729,031 B2 * | 5/2014 | Wadman | 514/21.4 |
| 2004/0101963 A1 | 5/2004 | Bibb et al. | |
| 2005/0271650 A1 | 12/2005 | Freimark et al. | |
| 2009/0203583 A1 | 8/2009 | Wadman et al. | |
| 2010/0048459 A1 | 2/2010 | Boakes et al. | |
| 2010/0168410 A1 | 7/2010 | Cade et al. | |
| 2010/0179207 A1 * | 7/2010 | Wadman | 514/414 |
| 2010/0261638 A1 | 10/2010 | Wadman | |
| 2011/0294723 A1 | 12/2011 | Wadman | |
| 2011/0306091 A1 | 12/2011 | Boakes et al. | |
| 2012/0277145 A1 | 11/2012 | Wadman | |
| 2012/0302728 A1 | 11/2012 | Dawson | |
| 2012/0309676 A1 * | 12/2012 | Wadman et al. | 514/2.3 |

FOREIGN PATENT DOCUMENTS

| | | |
|---|---|---|
| DE | 19745583 | 4/1999 |
| EP | 0195359 | 9/1986 |
| EP | 0572942 | 12/1993 |
| EP | 0700998 | 3/1996 |
| EP | 1646646 | 3/2007 |
| WO | WO 91/07949 | 6/1991 |
| WO | WO 91/11172 | 8/1991 |
| WO | WO 94/02518 | 2/1994 |
| WO | WO 97/00694 | 1/1997 |
| WO | WO 98/55148 | 12/1998 |
| WO | WO 02/00196 | 1/2002 |
| WO | WO 02/088367 | 11/2002 |
| WO | WO 02/103010 | 12/2002 |
| WO | WO 03/099862 | 12/2003 |
| WO | WO 2004/033706 | 4/2004 |
| WO | WO 2005/093069 | 10/2005 |
| WO | WO 2006/080920 | 8/2006 |
| WO | WO 2007/036706 | 4/2007 |
| WO | WO 2007/083112 | 7/2007 |
| WO | WO 2007083112 A2 * | 7/2007 |
| WO | WO 2008/151434 | 12/2008 |
| WO | WO 2009/010763 | 1/2009 |
| WO | WO 2009/010765 | 1/2009 |
| WO | WO 2010/058238 | 5/2010 |
| WO | WO 2010/082018 | 7/2010 |

(Continued)

OTHER PUBLICATIONS

"Designing Custom Peptides," from SIGMA Genosys, pp. 1-2, Accessed Dec. 16, 2004.
"Treatment of Clostridium difficile—Associated Disease (CDAD)," Obstetrics and Gynecology, 109(4):993-995 (2007).
Altena et al., "Biosynthesis of the lantibiotic mersacidin: organization of a type B lantibiotic gene cluster," Applied and Environmental Microbiology, 66(6):2565-2571 (2000).
Appleyard et al., "NVB302 : Gastrointestinal Stability and in vivo Activity in the Hamster Cecitis Model for Clostridium difficile Infection," Poster F1-1520, 49th ICAAC, Sep. 12-15, 2009, San Francisco, USA.

(Continued)

*Primary Examiner* — Julie Ha
*Assistant Examiner* — Kristina M Hellman
(74) *Attorney, Agent, or Firm* — Morgan, Lewis & Bockius LLP

(57) ABSTRACT

A liquid colloidal pharmaceutical formulation of a type B lantibiotic for infusion or direct injection is described, the formulation being clear of visual particulates and comprising a type B lantibiotic or a salt thereof, an isotonic aqueous solution comprising a sugar alcohol and optionally a buffer.

25 Claims, 6 Drawing Sheets

(56) References Cited

FOREIGN PATENT DOCUMENTS

Figure 1:
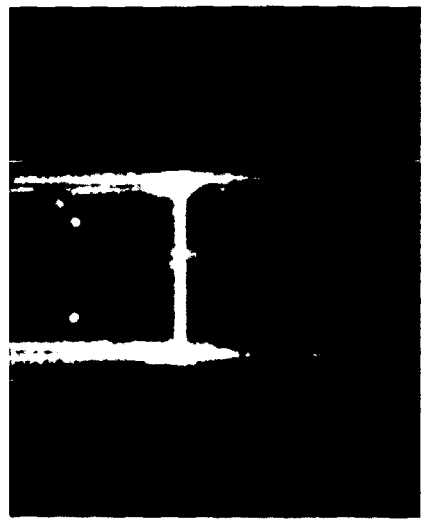
Figure 1:
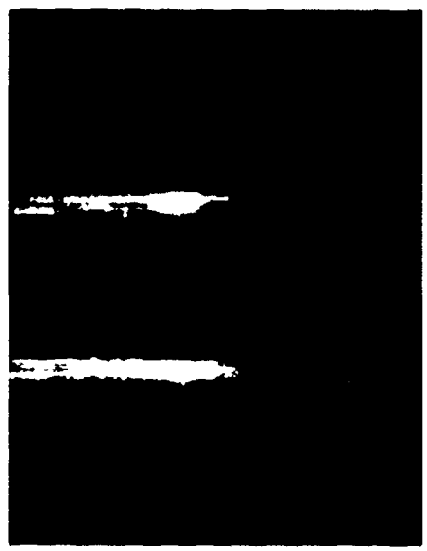
Figure 1:

| WO | WO 2010/082019 | 7/2010 |
|---|---|---|
| WO | WO 2010/089544 | 8/2010 |
| WO | WO 2011/095768 | 8/2011 |
| WO | WO 2011/095769 | 8/2011 |
| WO | WO 2012/007711 | 1/2012 |

OTHER PUBLICATIONS

Appleyard et al., "NVB302: A Narrow Spectrum Antibiotic under Development for the Treatment of Clostridium difficile Infection," Poster F1-1517, 49th ICAAC, Sep. 12-15, 2009, San Francisco, USA.

Arioli et al., "Gardimycin, a new anitbiotic from *Actinoplanes*: III. Biological properties" The Journal of Antibiotics, 29(5):511-515 (1976).

Berendsen, "A Glimpse of the Holy Grail?," Science, 282: 642-643 (1998).

Berge et al., "Pharmaceutical salts," Journal of Pharmaceutical Sciences, 66(1):1-19 (1977).

Bierbaum et al., "Cloning, sequencing and production of the lantibiotic mersacidin," FEMS Microbiology Letters, 127:121-126 (1995).

Bierman et al., "Plasmid cloning vectors for the conjugal transfer of DNA from *Escherichia coli* to *Streptomyces* spp.," Gene, 116(1): 43-49 (1992).

Boakes et al., "Organization of the biosynthetic genes encoding deoxyactagardine B (DAB), a new lantibiotic produced by *Actinoplanes liguariae* NCIMB41362," The Journal of Antibiotics, 63:351-358 (2010).

Boakes et al., "Organization of the genes encoding the biosynthesis of actagardine and engineering of a variant generation system," Molecular Microbiology, 72(5):1126-1136 (2009).

Bradley et al. "Limits of cooperativity in a structurally modular protein: Response of the notch ankyrin domain to analogous alanine substitutions in each repeat," J. Mol. Biol., 324: 373-386 (2002).

Britton et al., "Genome-Wide Analysis of the Stationary-Phase Sigma Factor (Sigma-H) Regulon of *Bacillus subtilis*," Journal of Bacteriology, 184(17):4881-4890 (2002).

Castiglione et al., "A novel lantibiotic acting on bacterial cell wall synthesis produced by uncommon actinomycete *Planomonospora* sp.," Biochemistry, 46:5884-5895 (2007).

Chatterjee et al., "Biosynthesis and Mode of Action of Lantibiotics," Chem. Rev. 105:633-683 (2005).

Clostridial intra-abdominal infections from Merck Manual, http://merckmanual.com/professional/sec15/ch189/ch189f.html, pp. 1-2, Accessed Aug. 10, 2011.

Clostridium difficile-induced diarrhea from Merck Manual, http://merckmanual.com/professional/sec15/ch189e.html, pp. 1-2, Accessed Aug. 10, 2011.

Cole et al., "Anti-infective innovations: highlights from the 49th Interscience Conference on Antimicrobial Agents and Chemotherapy (ICAAC)," Drugs of the Future, 34(12):1005-1028 (2009).

Coronelli et al., "Gardimycin, A New Antibiotic From Actinoplanes: II. Isolation and preliminary characterization," Journal of Antibiotics, 29(5):507-510 (1976).

Cotter et al., "Bacterial lantibiotics: strategies to improve therapeutic potential," Current Protein Peptide Science, 6(1):61-75 (2005).

Dabard et al., "Ruminococcin A, a new lantibiotic produced by a *Ruminococcus gnavus* strain isolated from human feces," Appl. Environ. Microbiol., 67:4111-4118 (2001).

Dawson, "Lantibiotics as antimicrobial agents," Expert Opinion on Therapeutic Patents, Informa Healthcare, GB, 17(4):365-369 (2007).

de Vos et al., "Maturation pathway of nisin and other lantibiotics: post-translationally modified antimicrobial peptides exported by gram-positive bacteria," Molecular Micobiology, 17(3):427-437 (1995).

Definition of moiety, from http://dictionary.reference.com/browse/moiety, pp. 1-3, Accessed Aug. 26, 2010.

Dower et al., "High efficiency transformation of *E. coli* by high voltage electroporation," Nucleic Acids Research, 16(13):6127-6145 (1988).

European Search Report issued in European Patent Application No. EP 10000424 dated Apr. 21, 2010.

Examination Report for New Zealand Patent Application No. 569486 dated Apr. 27, 2010.

Examination Report for New Zealand Patent Application No. 569486 dated Mar. 10, 2011.

Fleisher et al., "Improved oral drug delivery: solubility limitations overcome by the use of prodrugs," Advanced Drug Delivery Reviews, 19(2):115-130 (1996).

Flett et al., "High efficiency intergeneric conjugal transfer of plasmid DNA from *Escherichia coli* to methyl DNA-restricting Streptomycetes," FEMS Microbiology Letters, 155(2): 223-229 (1997).

Fukase et al., "Synthetic study of peptide antibiotic nisin. V. Total synthesis of nisin," Bull. Chem. Soc. Jpn., 65:2227-2240 (1992).

Fumi et al., "Rifaximin treatment for symptoms of irritable bowel syndrome," The Annals of Pharmacotherapy, 42:408-412 (2008).

Gardiner et al., "Fate of the Two-Component Lantibiotic Lacticin 3147 in the Gastrointestinal Tract," Applied and Environmental Microbiology, 73(21):7103-7109 (2007).

Gravesen et al., "pbp2229-Mediated nisin resistance mechanism in *Listeria monocytogenes* confers cross-protection to class IIa bacteriocins and affects virulence gene expression," Applied and Environmental Microbiology, 70(3): 1669-1679 (2004).

Guder et al., "Role of the single regulator MrsR1 and the two-component system MrsR2/K2 in the regulation of mersacidin production and immunity," Applied and Environmental Microbiology, 68(1):106-113 (2002).

Guiotto et al., "PEGylation of the antimicrobial peptide nisin A: problems and perspectives," Il Farmaco, 58(1):45-50 (2003).

Gust et al., "PCR-targeted Streptomyces gene replacement identifies a protein domain needed for biosynthesis of the sesquiterpene soil odor geosmin," PNAS, 100(4): 1541-1546 (2003).

Gust et al., "λ Red-mediated genetic manipulation of antibiotic-producing Streptomyces," Advances in Applied Microbiology ,54:107-128 (2004).

Han, "Advances in characterization of pharmaceutical hydrates," Trends in Bio/Pharmaceutical Industry, 25-29 (Mar. 2006).

Heinzelmann et al., "A glutamate mutase is involved in the biosynthesis of the lipopeptide antibiotic friulimicin in Actinoplanes friuliensis," Antimicrobial Agents and Chemotherapy, 47(2): 447-457 (2003).

Hilger et al., "Differential binding of IgG and IgA antibodies to antigenic determinants of bovine serum albumin," Clin. Exp. Immunol., 123:387-394 (2001).

Holtsmark et al., "Purification, Characterization, and Gene Sequence of Michiganin A, an Actagardine-Like Lantibiotic Produced by the Tomato Pathogen *Clavibacter michiganensis* subsp. *michiganensis*," Applied and Environmental Microbiology, 72(9):5814-5821 (2006).

International Preliminary Report on Patentability in PCT/GB2010/000043 dated Apr. 14, 2011.

International Preliminary Report on Patentability in PCT/GB2010/000042 dated Apr. 19, 2011.

International Preliminary Report on Patentability in PCT/GB2010/000188 dated Apr. 19, 2011.

International Search Report and Written Opinion for PCT/GB2010/000042 dated May 20, 2010.

International Search Report and Written Opinion for PCT/GB2010/000188 dated May 20, 2010.

International Search Report and Written Opinion for PCT/GB2010/000043 dated Mar. 29, 2010.

Jack et al., "The genetics of lantibiotic biosynthesis," Bioessays, 17(9):793-802 (1995).

Kettenring et al., "Sequence determination of actagardine, a novel lantibiotic, by homonuclear 2D NMR spectroscopy," J. Antibiot., 43(9):1082-1088 (1990).

Lonetto et al., "The sigma 70 family: sequence conservation and evolutionary relationships," Journal of Bacteriology, 174(12): 3843-3849 (1992).

(56) References Cited

OTHER PUBLICATIONS

Louie et al., "A phase 2 study of the toxin binding polymer tolevamer in patients with C. difficile associated diarrhoea," Proceedings of 14th European Congress of Clinical Microbiology and Infectious Diseases, Prague Congress Centre, Prague, Czech Republic, P548 (May 1-4, 2004).
Louie et al., "Tolemaver (GT160-246) binds Clostridium cytotoxins A/B and is associated with restoration of components of the anaerobic intestinal microflora during treatment of C. difficileassociated diarrhoea," Proceedings of 14th European Congress of Clinical Microbiology and Infectious Diseases, Prague Congress Centre, Prague, Czech Republic, P855 (May 1-4, 2004).
Malabarba et al., "Physico-chemical and biological properties of actagardine and some acid hydrolysis products," The Journal of Antibiotics, 38(11):1506-1511 (1985).
Malabarba et al., "Synthesis and biological activity of some amide derivatives of the lantibiotic actagardine," The Journal of Antibiotics, 43(9):1089-1097 (1990).
Marahiel et al., "Regulation of peptide antibiotic production in Bacillus," Molecular Microbiology, 7(5):631-636 (1993).
McClerren et al., "Discovery and in vitro biosynthesis of haloduracin, a two-component lantibiotic" PNAS, 103(46):17243-17248 (2006).
Miner et al., "Steroid-refractory ulcerative colitis treated with corticosteroids, metronidazole and vancomycin: a case report," BMC Gastroenterology 5:3 (2005).
Ngo et al. "Computational Complexity, Protein Structure Prediction, and the Levinthal Paradox," The Protein Folding Problem and Tertiary Structure Prediction, K. Merc JT. and S. Le Grand Edition, 491-495 (1994).
Non-final office action issued in U.S. Appl. No. 12/686,135 dated Apr. 28, 2011.
Notice of Allowance mailed in U.S. Appl. No. 12/161,221 dated May 12, 2011.
Office Action issued in Chinese Application No. 200780006748.0 dated Mar. 23, 2011 (Translation included).
Office Action issued in European Patent Application No. 07704921.1 dated Aug. 30, 2010.
Office Action issued in European Patent Application No. 07704921.1 dated Apr. 7, 2010.
Office Action issued in European Patent Application No. 10000424.1 dated May 19, 2011.
Office Action issued in European Patent Application No. 10000424.1 dated Jan. 25, 2013.
Office Action issued in European Patent Application No. 10700336.0 dated May 3, 2012.
Office Action issued in European Patent Application No. 10702536.3 dated May 11, 2012.
O'Sullivan et al., "High- and low-copy-number Lactococcus shuttle cloning vectors with features for clone screening," Gene, 137:227-231 (1993).
Parenti et al., "Gardimycin, a new antibiotic from Actinoplanes. I. Description of the producer strain and fermentation studies," The Journal of Antibiotics, 29(5):501-506 (1976).
Rea et al., "Antimicrobial activity of lacticin 3147 against clinical Clostridium difficile strains," Journal of Medical Microbiology, 56:940-946 (2007).
Rey et al., "Complete genome sequence of the industrial bacterium Bacillus licheniformis and comparisons with closely related Bacillus species," Genome Biology, 5(10):R77 (2004).
Rudinger J, "Characteristics of the amino acids as components of a peptide hormone sequence," Peptide Hormones, JA Parsons Edition, University Park Press, Jun. 1976, pp. 1-7.
Sahl et al., "Lantibiotics: Biosynthesis and biological activities of uniquely modified peptides from gram-positive bacteria," Ann. Rev. Microbiology, 52:41-79 (1998).
Schinzel et al. "The phosphate recognition site of *Escherichia coli* maltodextrin phosphorylase," FEBS, 286(1,2): 125-128 (1991).
Somma et al., "Gardimycin, a new antibiotic inhibiting peptidoglycan synthesis," Antimicrobial Agents and Chemotherapy, 11(3):396-401 (1977).
Szekat et al., "Construction of an expression system for site-directed mutagenesis of the lantibiotic mersacidin," Applied and Environmental Microbiology, 69(7):3777-3783 (2003).
Translation of Israeli Examination Report for Israeli Patent Application No. 192446 dated Apr. 22, 2010.
Turner et al., "Solution structure of plantaricin C, a novel lantibiotic," Eur. J. Biochem., 264:833-839 (1999).
Turtell et al., "The use of nisin in cheesemaking. Chapter 5: International acceptance of nisin as a food preservative," Bulletin of the Int. Dairy Fed., 329:20-23 (1988).
Ugurlu et al., "Colonic delivery of compression coated nisin tablets using pectin/HPMC polymer mixture," Eur. J. Pharm. Biopharm., 67:202-210 (2007).
van Kraaij et al., "Lantibiotics: biosynthesis, mode of action and applications," Nat. Prod. Rep., 16:575-587 (1999).
Vertesy et al., "Ala(0)-actagardine, a new lantibiotic from cultures of *Actinoplanes liguriae* ATCC 31048," Journal of Antibiotics, Japan Antibiotics Research Association, 52(8):730-741 (1999).
Vippagunta et al., "Crystalline solids," Advanced Drug Delivery Reviews, 48(1):3-26 (2001).
Voet et al., "Abnormal Hemoglobins," Biochemistry, Second Edition, John Wiley & Sons, Inc., pp. 235-241 (1995).
Wadman et al., "NVB302: In vitro Activity Against Clostridium difficile and Intestinal Strains of Anaerobic Bacteria," Poster F1-1518, 49th ICAAC, Sep. 12-15, 2009, San Francisco, USA.
Widdick et al., "Cloning and engineering of the cinnamycin biosynthetic gene cluster from *Streptomyces cinnamoneus cinnamoneus* DSM 40005," PNAS, 100(7):4316-4321 (2003).
Wikipedia, the free encyclopedia, "Lanthionine," http://en.wikipedia.org/wiki/Lanthionine, (Nov. 2, 2011).
Written Opinion of the International Preliminary Examining Authority in PCT/GB2010/000043, dated Feb. 1, 2011.
Zimmerman et al., "The tetracyclic lantibiotic actagardine H-NMR and C-NMR assignments and revised primary structure," European Journal of Biochemistry, 228(3):786-797 (1995).
Zimmermann et al., "The three-dimensional solution structure of the lantibiotic murein-biosynthesis-inhibitor actagardine determined by NMR," Eur. J. Biochem., 246:809-819 (1997).

* cited by examiner

Example 1 in Glucose (10mg/ml)

Vancomycin in Glucose (10mg/ml)

Glucose

*Fixed exposures*

FORMULATIONS FOR INFUSION OF TYPE B LANTIBIOTICS

This application is related to GB 1013513.5 filed Aug. 11, 2010; the contents of which are incorporated herein by reference in their entirety.

The present invention relates to liquid formulations of type B lantibiotics and their derivatives for parenteral administration including formulations for infusion or direct injection, in particular, colloidal formulations of actagardine or deoxyactagardine compounds or derivatives thereof, liquid concentrates of said formulations (such as liquid concentrates for dilution with water for injection or an isotonic solution to provide a final formulation for infusion or direct injection) and/or lyophilised versions thereof (providing some or all of the components in a dry form) for reconstitution with water for injection or an isotonic solution. The disclosure also extends to processes for preparing the same and the use of the formulations in treatment, such as the treatment of a microbial infection, particularly gram positive bacteria infections, such as methicillin-resistant *Staphylococcus aureus* (MRSA) infection.

Type B lantibiotics have been known for a number of years and are globular in nature. In contrast type A lantibiotics are long flexible molecules.

At the time of writing no type B lantibiotics had progressed to gaining regulatory approval for the treatment of human beings. Often the suggested delivery of the type B lantibiotic is oral or topical. This is because a number of the molecules have poor solubility/physiochemical properties which render them difficult to formulate in a way that is suitable for parenteral administration, for example in Malabarba et al. (*The Journal of Antibiotics* November 1986 page 1506-1511) type B lantibiotics were formulated as a suspension in Methocell for subcutaneous injection.

Nevertheless, the inventors believe that in some instances it would be very useful to administrate a type B lantibiotic in the form of a product for dosing by infusion or by direct injection, for example when the infection is acute and/or cannot be treated by topical administration.

Saline is a commonly used vehicle for infusion or injection. However, it has been discovered that type B lantibiotics behave somewhat like proteins and in the presence of salt tend to precipitate or aggregate. Thus formulations of type B lantibiotics with a significant salt content are generally unstable or unsuitable for infusion or injection. Salt, when employed in this context, is intended to refer to sodium or potassium chloride. It will be clear reading the specification that salt is used in other contexts which does not relate to the use of sodium or potassium chloride.

The present invention relates to a formulation of a type B lantibiotic suitable for dosing by infusion or by direct injection.

SUMMARY OF THE INVENTION

Thus there is provided a liquid pharmaceutical formulation of a type B lantibiotic for infusion or direct injection comprising:

a type B lantibiotic or a salt thereof (such as a salt), an isotonic aqueous solution comprising a sugar alcohol (such as glycerol) and/or a saccharide and optionally a buffer, wherein the final formulation for infusion or direct injection is clear of particulates when observed by the naked eye.

In particular there is provided a liquid colloidal pharmaceutical formulation of a type B antibiotic for infusion or direct injection comprising:

a type B lantibiotic or a salt thereof (such as a salt)

an isotonic aqueous solution comprising a sugar alcohol (such as glycerol) and/or a saccharide and optionally a buffer, wherein the final formulation for infusion or direct injection is clear of particulates when observed by the naked eye.

BRIEF DESCRIPTION OF THE FIGURES

FIG. 1 is a series of photographs of two control formulations (glucose and vancomycin) and a formulation of Example 1, after a laser beam has been shone through a cuvette containing the same. For the formulation of Example 1 the beam is visible through the formulation due to light scattering (Rayleigh scatter) by the formulation. In contrast the beam is not visible in the control formulations. In each case the presence or absence of the beam in the samples is clearly visible to the naked eye.

FIG. 2 is a graph showing the change in the number of colony forming units in the thigh tissue of infected mice after treatment with Example 1 or vancomycin at various mg/kg dose levels FIG. 3 is a graph showing the dose dependent reduction in the bacterial counts in the thigh tissue of mice after treatment with Example 1 or vancomycin FIG. 4 is graph showing the change in the mean plasma concentration of Example 1 in mice plasma over time FIG. 5 shows photographs of formulations according to the invention FIG. 6 is a schematic representing the interaction between a lyophilised formulation, the liquid concentrate and the final formulation.

Surprisingly, the present inventors have established that a type B lantibiotic or a salt thereof can be formulated in sugar and/or sugar alcohol carriers for infusion or direct injection. In one embodiment the type B lantibiotic is employed in the form of a salt.

Infusion as employed herein is intended to refer to the administration of the large volumes of a formulation, for example 100 mL or more such as 300 to 500 mL, which in particular are administered intravenously. Formulations for infusion must be approximately isotonic. Direct injection is intended to refer to rapid administration of the formulation employing a syringe and needle or an automated pump, for example as employed for administering heparin. Generally the volumes administered are 5 to 25 mL such as 10 to 20 mL, delivered over a period of 1 to 5 minutes. Formulations for direct injection must be approximately isotonic.

Generally, the formulation is colloidal.

Thus there is provided a liquid pharmaceutical colloidal formulation of a type B lantibiotic for infusion or direct injection comprising:

a type B lantibiotic or a salt thereof (such as a salt), an isotonic aqueous solution comprising a sugar alcohol (such as glycerol) and/or a saccharide and optionally a buffer, wherein said formulation or a concentrate thereof can be filtered through a 0.2 micron filter, and the final formulation for infusion or direct injection is clear of particulates when observed by the naked eye.

The colloid formulation according to the present invention is distinguished from a solution by the fact that a polarised beam of light, such as from laser, shone through the formulation, for example held in a 1 cm cuvette, causes the formulation to scatter light visible to the naked eye therefrom, for example in the form of a beam. Whilst not wishing to be bound by theory, this luminous path may be known as a Tyndall beam or Rayleigh scatter, both of which are a result of the scattering of the light by the particles in the colloid.

In one embodiment the laser shone through the formulation has a wavelength of 200 nm.

Thus in one embodiment a luminous path (such as a Tyndall beam) is generated in/from the formulation when a beam of light is shone therethrough.

In a further independent aspect there is provided a pharmaceutical colloidal formulation of a type B lantibiotic for infusion or direct injection comprising:
    a type B lantibiotic salt,
    an isotonic aqueous solution comprising a sugar alcohol such as glycerol, and/or a saccharide, and
optionally a buffer, wherein the colloidal formulation comprises a phase of particulates or sols having an average size less than 200 nm.

DETAILED DESCRIPTION

Pharmaceutical colloidal formulations such as colloidal suspensions are acceptable for infusion to humans provided that they are stable and can be sterilised, for example the latter may be effected by filtering through a 0.2 µm filter. These filters are sufficiently small to prevent pathogens passing through them and therefore can be used to render formulations which have not been manufactured aseptically fit for administration parenterally to a human or animal.

Surprisingly the present inventors have found that certain salts of type B lantibiotics are more soluble than the corresponding parent compound and that these form stable colloidal formulations in aqueous isotonic sugar alcohol and/or saccharide solutions. Interestingly, the same compounds do not form stable formulations in isotonic saline solutions. In particular the formulations of the present disclosure are free from visible particulates, which is vitally important for formulations for parenteral administration.

Chapter 1 of the United States Pharmacopeia, Injections, under "Foreign and Particulate Matter," states the following: "Each final container of all parenteral preparations shall be inspected to the extent possible for the presence of observable foreign and particulate matter (hereinafter termed "visible particulates") in its contents. The inspection process shall be designed and qualified to ensure that every lot of all parenteral preparations is essentially free from visible particulates. Qualification of the inspection process shall be performed with reference to particulates in the visible range of a type that emanate from the manufacturing or filling process. Every container whose contents show evidence of visible particulates shall be rejected. The term "essentially free" represents one of the more difficult challenges in parenteral product development and manufacturing, and there is an ongoing need to develop a quantitative and scientifically defensible definition of what "essentially free" means. The text above, in addition to introducing the term "essentially free", contains verbiage that reflects the point of view of most of the published scientific literature and draft guidelines on visual inspection of parenterals; that is, it is focused on visual inspection in a manufacturing environment, where the primary concern is making valid accept/reject decisions for individual vials, cartridges, or syringes. Visual inspection in a product development environment may differ from visual inspection in manufacturing."

Thus visual inspection and particulates observed by the naked eye are relevant to the manufacture of parenteral formulations.

Visible to the naked eye in the context of the present specification is a reference to an observer having appropriate vision, or with correction such as glasses or contact lenses, and said observer is trained to performed the relevant visual inspection. The particulates when present will be visible to said observer when the formulation is inspected under appropriate conditions.

When formulated in isotonic saline, aggregation of the compounds can occur resulting in undesirable particulates in the preparation.

Isotonic as employed herein is intended to refer to a solution that is acceptable for parenteral administration, for example because it has approximately the same concentration of solutes as blood.

Hypertonic as employed herein is intended to refer to solutions having a higher concentration of solutes than blood.

Hypotonic as employed herein is intended to refer to solution having a lower concentration of solutes than blood.

In one embodiment the formulations have a low salt content, for example an inorganic salt content, such as a sodium chloride, potassium chloride or a combined salt content of 0.5% w/v or less, for example 0.3% w/v or less, such as 0.2% w/v or less, in particular 0.1% w/v or less.

The liquid formulations of the present invention (including concentrates) can be filtered through a 0.2 µm membrane filter.

Colloidal, as employed herein, is intended to refer to a polyphasic system comprising a dispersed phase and a continuous phase. The matter in the dispersed phase is characterised by submicroscopic dimensions, for example less than 500 nm, such as in the range 5 to 200 nm.

In one embodiment the formulation is a colloidal dispersion.

The definition of colloid dispersion as employed herein is intended to include a colloidal suspension and a colloidal emulsion, as appropriate. In a colloidal suspension, solid particles in the colloidal range are dispersed in a liquid. In a colloidal emulsion, liquid droplets and/or liquid crystals are dispersed in a liquid.

In one embodiment the formulation is a colloidal suspension formulation.

In one embodiment the dispersed phase comprises particulates or sols.

Sols are lyophobic (solvent hating) suspensions of solid particles (1 to 1,000 nm in size) in a liquid.

In one embodiment the average particles are 200 nm or less in at least one dimension, for example in the range 10 nm to 190 nm, such as 20, 30, 40, 50, 60, 70, 80, 90, 100, 110, 120, 130, 140, 150, 160, 170, 180, 190 nm.

In one embodiment at least 50%, such as 60, 70, 80, 90, 91, 92, 93, 94, 95, 96, 97, 98, 99% or substantially all the particles have an average size in the range.

Particle size analysis can be performed using methods known in the art, for example a Malvern Mastersizer 2000 particle size analyser or Zetasizer Nano S may be suitable for the analysis.

Generally the continuous phase is liquid, in particular it is aqueous and in this case the colloids are termed hydrocolloids. Thus the colloids of the present invention are hydrocolloids.

In one embodiment the formulation is a fluid colloidal system comprising one or more, such as 1 or 2, sol components, for example the lantibiotic B may be in the form a peptide sol.

Whilst the inventors suspect the colloid of the present invention is a solid/liquid colloidal suspension it may nevertheless be a colloidal emulsion.

The present disclosure also provides a formulation in the form of a liquid concentrate. The liquid concentrate formulations provide some or all of the components of a final formulation but in a smaller volume. The liquid concentrates will comprise at the least the type B lantibiotic or salt thereof for example in water or other suitable aqueous solution. The liquid concentrates will generally further comprise at least one excipient. In at least one embodiment the liquid concentrate will contain all the final excipients but in a smaller volume than employed in the final liquid formulation.

Generally a liquid concentrate will have a type B lantibiotic or salt thereof concentration above 20 mg/mL such as in the range 21 mg/mL to 100 mg/mL.

Generally the liquid concentration of the type B lantibiotic or salt thereof in the liquid concentrate formulation is in the range 40-75 mg/mL, such as 50 mg/mL. Generally the liquid concentrate will not be suitable for administration to a patient, without further dilution with water for injection or a suitable aqueous solution.

Thus concentrates of formulations for dilution prior to infusion (or concentrates for dilution prior to direct injection), as employed herein, refers to liquid formulations containing all or the majority of the ingredients of the final formulation (including the type B lantibiotic or a salt thereof [such as a salt]) but in a smaller volume than that used for the final parenteral administration.

When the concentrate contains all the ingredients it simply requires diluting with water for injection to generate the final formulation, suitable for parenteral administration to a patient. Thus in one embodiment the concentrate is hypertonic. Concentrates that contain the majority of ingredients is intended to refer to concentrates that require dilution with a sterile isotonic solution, such as a saccharide solution (for example a solution of a monosaccharide such as glucose) to or a solution of a sugar alcohol such as a mannitol or sorbitol solution to generate a final liquid formulation.

In one embodiment the concentrate is hypotonic.

In one embodiment the concentrate formulation is hypertonic because it contains all the ingredients of the final formulation.

All the ingredients of the final formulation, except for the lantibiotic or other pharmaceutically active ingredient, are referred to herein as excipients.

Final formulation as employed herein is intended to refer to final formulations for infusion or direct injection, which are suitable for administration to a patient.

In one embodiment the liquid concentrate comprises:
a type B lantibiotic or salt thereof (such as salt) for example at a concentration described herein such as 50 mg/mL;
3-10% w/w or w/v mannitol, sorbitol, glucose or a combination thereof (such as 4-6%)
optionally 1-3% w/w or w/v of glycerol, and
a buffer or HCl
wherein the concentrate is suitable for dilution with water for injection to provide an isotonic solution.

In one embodiment the liquid concentrate comprises:
a type B lantibiotic or salt thereof (such as salt) for example at a concentration described herein such as 50 mg/mL;
optionally 1-3% w/w or w/v of glycerol, and
a buffer or HCl
wherein the concentrate is suitable for dilution with a solution of glucose, mannitol, sorbitol or a combination thereof to provide an isotonic solution.

In one embodiment a liquid concentrate formulation according to the present disclosure is diluted with water, a glucose solution, a mannitol solution, a sorbitol solution or a combination thereof, to provide an isotonic formulation suitable for parenteral administration to a patient.

The values of w/w and w/v percentages in the concentrate are in fact by reference to the final formulation. The percentage of the ingredients in the concentrate will be higher than than stated.

In one embodiment mannitol or a mannitol solution is employed.

In one embodiment sorbitol or a sorbitol solution is employed.

In one embodiment glucose or a glucose solution is employed, such as 5% glucose.

In one embodiment the liquid concentrate comprises a type B lantibiotic or a salt thereof, glucose and a pH adjusting agent selected from a buffer or HCl. For example the glucose is present in an amount to provide a concentration of 5% w/w or w/v or less in a final formulation. This concentrate may be diluted with water and/or an isotonic diluent to provide an isotonic final formulation.

In one embodiment the liquid concentrate comprises a type B lantibiotic or a salt thereof, a pH adjusting agent selected from a buffer or HCl, and one or more excipients selected from mannitol, glycerol, sorbitol or a combination thereof. This concentrate requires dilution with water.

In one embodiment the liquid concentrate comprises a type B lantibiotic or a salt thereof and a pH adjusting agent selected from a buffer or HCl. This concentrate requires dilution with an isotonic diluent.

In one embodiment, a liquid concentrate formulation is diluted to be isotonic with glucose to provide an isotonic formulation suitable for parenteral administration, for example standard glucose for infusion, i.e. 5% glucose solution.

In one embodiment a liquid concentrate formulation according to the present disclosure is diluted with water for infusion or injection, to provide an isotonic formulation suitable for parenteral administration.

In one embodiment a liquid concentrate formulation according to the present disclosure is diluted with a mannitol solution or a sorbitol solution (such as a mannitol solution), to provide an isotonic formulation suitable for parenteral administration to a patient.

A derivative of the type B lantibiotic as employed herein is intended to refer to: a naturally occurring mutant, wherein one or two amino acids are added, deleted or changed, such as Ala (0)-actagardine, a recombinantly prepared mutant where one to four amino acids are added, deleted of changed, and semisynthetic compounds of either of the same wherein the N and/or C-terminus of the peptide has been modified employing medicinal/synthetic organic chemistry techniques. Additionally or alternatively, the semisynthetic compounds may include those where the amino acid side chain functionality, such as amino or carboxy functionality, has been modified employing medicinal/synthetic organic chemistry techniques The present invention allows a robust formulation to be prepared for direct injection or infusion.

In one embodiment there is provided a lyophilised formulation which, for example, contains all the final ingredients of the formulation in a dry form, to which water for injection can be introduced to reconstitute the dry ingredients to provide a final isotonic formulation for parenteral administration to a patient.

In one embodiment there is provided a lyophilised formulation which provides ingredients which can be reconstituted with a suitable solution such as a glucose solution, a mannitol solution, a sorbitol solution or a combination thereof, to provide a final isotonic formulation for parenteral administration to a patient.

Lyophilised formulations are prepared by lyophilisation.

Concentrates containing the ingredients and suitable for dilution and lyophillised forms of parenteral formulations, which require reconstitution prior to direct injection and/or dilution prior to infusion, are also suitably stable for the intended purpose.

Alternatively the dry ingredients of the formulation can be prepared in the form of a solid form by evaporation of solvents from the ingredient or methods such as spray-drying or supercritical drying.

Supercritical drying is a process to remove liquid in a precisely controlled way. Fluids suitable for supercritical drying include carbon dioxide (critical point 304.25 K at 7.39 MPa or 31.1° C. at 1072 psi) and freon (=300 K at 3.5-4 MPa or 25-0° C. at 500-600 psi).

In most such processes, acetone is first used to wash away all water, exploiting the complete miscibility of these two fluids. The acetone is then washed away with high pressure liquid carbon dioxide, the industry standard now that freon is unavailable. The liquid carbon dioxide is then heated until its temperature goes beyond the critical point, at which time the pressure can be gradually released, allowing the gas to escape and leaving a dried product.

In one embodiment the lypohilised formulation is diluted with glucose, for example standard glucose, i.e. 5% glucose solution to provide a liquid concentrate or isotonic formulation suitable for parenteral administration.

In one embodiment the lypohilised formulation is diluted with a mannitol solution or a sorbitol solution (such as a mannitol solution) to provide a liquid concentrate or isotonic formulation suitable for parenteral administration.

In one embodiment the lypohilised formulation is diluted with water for infusion or injection to provide a liquid concentrate or an isotonic formulation suitable for parenteral administration.

Thus in one aspect there is provided a method of providing a final formulation by diluting or reconstituting a formulation described herein.

In addition or alternatively the present invention provides a method for optimising the stability of the formulation.

Providing the lantibiotic type B salt in an aqueous carrier selected from glycerol, and/or a saccharide allows a suitably fine hydrocolloid suspension to be formed. However, when isotonic saline solutions are used as the carrier then the colloidal particles flocculate and form aggregates which precipitate out of solution and are not suitable for infusion or direct injection.

Surprisingly the inventors established that a colloidal formulation with suitable characteristics for infusion, i.e. which can be filtered through a 0.2 μm filter can be prepared in an isotonic aqueous solution comprising a sugar alcohol such as glycerol and/or a saccharide. It is expected that the average particle size of the dispersed phase of the type B lantibiotic and/or other components of the colloidal system is smaller than 0.2 μm.

In one embodiment the formulation is a final formulation suitable for infusion, for example is provided with the lantibiotic concentration in the range 1 to 50, such as 5 to 20 mg/mL, in particular 2, 3, 4, 5, 6, 7, 8, 9 or 10 mg/mL.

In one embodiment the formulation is suitable for direct injection, for example is provided at a concentration in the range 10-100 mg/mL, such as about 20 mg/mL.

A sugar alcohol (also known as a polyol, polyhydric alcohol, or polyalcohol) is a hydrogenated form of carbohydrate, whose carbonyl group (aldehyde or ketone, in the case of a reducing sugar) has been reduced to a primary or secondary hydroxyl group.

In one embodiment the formulation comprises a sugar alcohol, such as glycol, glycerol, erythritol, threitol, arabitol, xylitol, ribitol, mannitol, sorbitol, dulcitol, iditol, isomalt, maltitol, lacitol or polyglycitol.

Sugar alcohol as employed herein is not intended to refer to a cyclodextrin such as hydroxypropyl-β-cyclodextrin.

In one embodiment the saccharide is a sugar, for example a simple sugar (a monosaccharide), such as selected from ketotriose (dihydroxyacetone), aldotriose (glyceraldehyde) ketotetrose (erythrulose), aldotetroses (erythrose, threose), ketopentose (ribulose, xylulose), aldopentose (ribose, arabinose, xylose, lyxose), deoxy sugar (deoxyribose), ketohexose (psicose, fructose, sorbose, tagatose), aldohexose (allose, altrose, glucose, mannose, gulose, idose, galactose, talose), deoxy sugar (fucose, fuculose, rhamnose), heptose (sedoheptulose), octose and nonose (neuraminic acid).

In one embodiment the saccharide is a disaccharide, for example sucrose, lactose, maltose, trehalose, turanose or cellobiose.

In one embodiment the saccharide is a trisaccharide, for example raffinose, melezitose or maltotriose.

In one embodiment the saccharide is a polysaccharide, for example glucose, dextrin, beta-glucan, maltodextrin, In one embodiment the saccharide/sugar alcohol content of the final formulation is in the range 1 to 10% w/w, for example 2, 3, 4, 5, 6, 7, 8 or 9% w/w, such as 5 or 3.3%.

In one embodiment the formulation comprises an aqueous sugar solution for example comprising mannitol, sorbitol, glucose, and/or sucrose or combination thereof.

In one embodiment the sugar alcohol is sorbitol.

In one embodiment the sugar alcohol is mannitol.

In one embodiment the formulation comprises aqueous glycerol, for example about 1 to 5% w/w, for example 2, 3, 4% w/w, such as 2.6% w/w of the final formulation.

In one embodiment the saccharide/sugar employed is a non-reducing sugar. A non-reducing sugar as employed herein is a sugar without an aldehyde or ketone functional group therein. An example of a reducing sugar is glucose. Examples of non-reducing sugars are sucrose and trehalose.

In one embodiment the isotonic aqueous carrier comprising glycerol and a saccharide.

In one embodiment the formulation comprises:
2.6% w/w glycerol, and/or
5% w/w mannitol, or
5 to 5.5% w/w sorbitol (5% w/w anhydrous sorbitol or 5.5% w/w sorbitol hemihydrate, or
9% w/w sucrose.

Alternatively a combination of two or three of mannitol, sorbitol or sucrose may be employed.

In one embodiment, for example where the lantibiotic compound employed is monobasic, the salt is derived from an amino sugar or amino alcohol. Providing the lantibiotic as a salt of an amino alcohol in some instances assists in forming a dispersion of the lantibiotic in the carrier.

Examples of amino alcohols include ethanolamine, glucosamine and glucamines such as N-methylglucamine, N-ethylglucamine, in particular the N-methylglucamine or N-ethylglucamine.

In one embodiment the salt has a stoichiometry of 1:1 or 2:1 with the type B lantibiotic employed.

In one embodiment between 1 to 3 equivalents (such as about 2 equivalents) of the amino alcohol is/are employed in the formulation with the type B lantibiotic to form a salt. In particular, 2 or 3 equivalents of the amino alcohol are employed in forming the salt (relative to the type B lantibiotic). Thus the salt formed may comprise a true salt, for example it may comprise a salt in admixture optionally with the excess of the amino alcohol, in particular prepared by lyophillising the amino alcohol with a type B lantibiotic in a pre-treatment step. Thus in one embodiment the type B lantibiotic salt is in the form of a salt complex, for example wherein the amino alcohol is in a non-stoichiometric ratio with the type B lantibiotic.

In one embodiment the amino alcohol and type B lantibiotic are in the ratio 2:1 respectively, in the formulation.

In one embodiment 1, 2 or 3 molar equivalents of the amino alcohol (c.f. the lantibiotic amount) may be added in admixture to the formulation in addition or as an alternative to the pre-formed salt.

In one embodiment the lantibiotic salt may be formed in situ, during the preparation of the liquid formulation by adding the parent lantibiotic compound to the formulation and also adding the amino alcohol thereto in the required ratio.

For some embodiments, the formulation may also comprise a cyclodextrin with the proviso that the formulation does not consist of deoxyactagardine 3,5-dichlorobenzylamine meglumine salt, 15% hydroxylpropyl-β-cyclodextrin, 4.4% glucose and 0.5 mM $KH_2PO_4$.

Thus in one embodiment the formulation does not comprise glucose and hydroxylpropyl-β-cyclodextrin.

Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO 91/11172, WO 94/02518 and WO 98/55148.

In one embodiment the formulation comprises up to 15% w/w cyclodextrin.

In one embodiment the formulation according to the present disclosure is substantially free of cyclodextrin, in particular contains 0.1% w/v or less such as 0.01% w/v or less cyclodextrin.

In one embodiment the formulation may comprise polyethylene glycol, for example PEG 300, such as 6.73% w/w, PEG 400, such as 8.5% w/w or PEG 1500, such as 10% w/w.

In one embodiment the formulation comprises propylene glycol, for example 2.1% w/w.

% w/w as employed herein refers to the mass of the ingredient employed in the formulation as a % of the final formulation mass. % w/v as employed herein refers to the mass of the ingredient such as dry ingredient of the formula in a given volume of liquid carrier/excipient of the formulation.

In one embodiment the formulation comprises an antioxidant, for example ascorbic acid, glutathione, vitamin E and/or citric acid.

In one embodiment the formulation comprises a surfactant, for example a non-ionic surfactant, including surface active polymers, or phospholipids. Examples of non-ionic surfactants include sterols such as cholesterol and cholesterol esters; synthetic non-ionic surfactants such as ethoxylated alcohols, ethoxylated alkyl phenols, ethoxylated ethers and esters, fatty alcohols, fatty acid esters, ethoxylated fatty acids, ethoxylated sorbitan fatty acid esters such as polysorbates, polypropylene-polyethylene block copolymers such as poloxamers. Examples of phospholipids are naturally occurring phospholipids such as egg and soy lecithin, synthetic or semisynthetic phospholipids such as phosphatidylcholines, phosphatidylethanolamines and phosphatidylglycerols, ethoxylated phospholipids and glycolipids.

In one embodiment the formulation comprises a buffer, for example a phosphate buffer or citrate buffer. In one embodiment a buffer, such as a phosphate buffer is employed, for example to adjust the pH of the final formulation. Having said this the amounts of buffer employed may need to be controlled as high concentrations of buffer may cause aggregation.

In one embodiment the buffer concentration is 75 mM or less, for example 50 mM or less, such as 40 mM or less, in particular 30 mM or less, especially 5 mM or less.

In one embodiment the buffer concentration is 1.5% w/v or less, for example 1% w/v.

In one embodiment the formulation comprises a preservative.

In one embodiment the final pH of the formulation is in the range 7 to 9, for example 8 to about 8.5.

When the compound employed in the formulation is monobasic then a ratio in the range 1:1 to 2:1 amino alcohol residue:lantibiotic ratio is desirable. Generally the final pH of such a formulation will be above pH 7, for example 7 to 9, such as pH 8 or 8.5.

In one embodiment, for example when the compound employed in the formulation is dibasic then generally the final pH of the formulation will be below pH 7, for example 2.5 to 6, such as 3 to 4.

In one embodiment the zeta potential for the formulation is not in the range −30 to +30. In one embodiment the zeta potential is in the range 35 or more such as 35, 40, 45, 50, 55, 60 or more. In one embodiment the zeta potential is in the range −35 or less such as, −40, −45, −50, −55, −60 or less.

Sometimes thought of as a 'charge' measurement, zeta potential is used to assess the charge stability of a disperse system, and assist in the formulation of stable products. Zeta potential may be related to the surface charge in a simple system, but equally well may not. The zeta potential can even be of opposite charge sign to the surface charge. Nevertheless, the zeta potential seems to relate to charge interactions, and not simply charge at the surface.

The significance of the zeta potential is that its value can be related to the stability of colloidal dispersions. The zeta potential indicates the degree of repulsion between adjacent, similarly charged particles in a dispersion. For molecules and particles that are small enough a high zeta potential will confer stability, i.e. the solution or dispersion will resist aggregation. When the potential is low, attraction exceeds repulsion and the dispersion will break and flocculate. So, colloids with high zeta potential (negative or positive) are electrically stabilized while colloids with low zeta potentials tend to coagulate or flocculate.

Thus the zeta potential can be used to assess the effect of each additive in the formulation. Additives can have surprising effects; some materials typically described as dispersion agents have been known to reduce the zeta potential in particular formulations. It is not always possible to predict the effect or the magnitude of the effect of an additive. The zeta potential can also be used to increase shelf life by assessing the impact of product changes during storage, e.g. hydrolysis or the like.

Thus adjustment of one parameter of the formulation, such as pH can change the value of the zeta potential of the formulation, for example to bring it into an undesirable range. This change can be readjusted and in essence be compensated for to retain a desirable zeta potential by altering another parameter that also influences the potential.

Zeta potential is not measurable directly but it can be calculated using theoretical models and an experimentally-determined electrophoretic mobility or dynamic electrophoretic mobility. Zeta potential measurements can be taken by applying an electric field across the dispersion. Particles within the dispersion with a zeta potential will migrate toward the electrode of opposite charge with a velocity proportional to the magnitude of the zeta potential.

This velocity is measured using the technique of laser Doppler anemometry. The frequency shift or phase shift of an incident laser beam caused by these moving particles is measured as the particle mobility, and this mobility is converted to the zeta potential by inputting the dispersant viscosity, and the application of the Smoluchowski or Huckel theories. These theories are approximations useful for most applications. More recent models are available which can give a more exact conversion, but require more knowledge of the chemistry of the dispersion.

A Zetasizer Nano series may be employed to measure the Zeta potential. It uses second generation PALS (Phase Analysis Light Scattering), called M3PALS, to measure the particle velocity. Using phase analysis rather than frequency analysis is up to 1,000 times more sensitive to changes in particle mobility. This is particularly important when measuring samples at high ionic concentration, e.g. isotonic saline compositions.

Thus, whilst not wishing to be bound by theory it is thought that the value of the zeta potential is of importance rather than simply the pH or the ionic strength of the formulation.

A high ionic strength (a high concentration of ions in solution) resulting, for example from a high saline or sodium chloride content is thought to lead to instability in the formulations of the present invention, and may result in one or more components of the formulation crashing out of solution. This phenomenon may be as a result of salting out or colloidal ripening.

A high saline content (or sodium chloride content) may result in an increase in conductivity of the formulation in comparison to a corresponding formulation with a low saline (or sodium chloride) content.

Thus, in one aspect there is provided a method for measuring the stability and/or identifying an optimised formulation according to the disclosure.

Lantibiotics are a class of peptide antibiotics that contain polycyclic thioether amino acids as well as the unsaturated amino acids dehydroalanine and 2-aminoisobutyric acid. These characteristic cyclic thioether amino acids are composed of either lanthionine or methyllanthionine. Type B lantibiotics are globular and include compounds such as michaganin, mersacidin, actagardine, actagardine B, cinnamycin, deoxyactagardine and deoxyactagardine B.

In one embodiment the type B lantibiotic is mersacidin, actagardine, Ala(0)actagardine, actagardine B, deoxyactagardine, deoxyactagardine B, cinnamycin or a derivative thereof.

In one embodiment the type B lantibiotic has the formula (I):

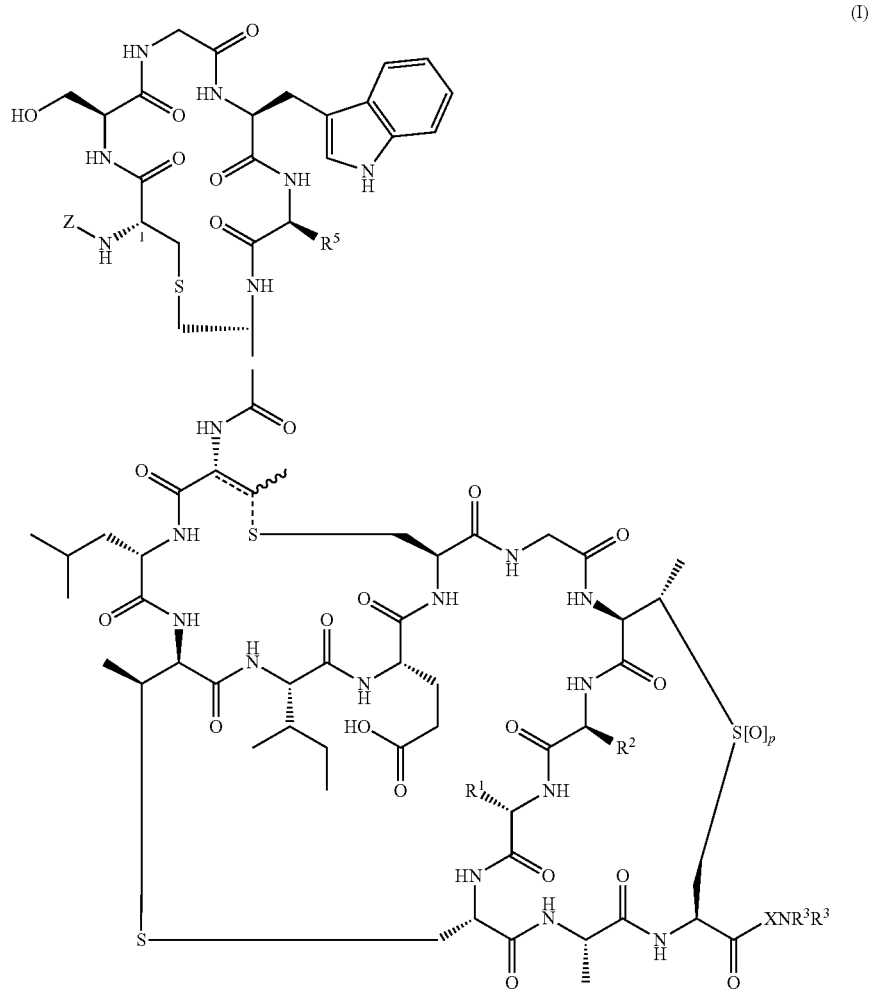

$R^1$ together with the carbon to which it is attached and the alpha-nitrogen and alpha-carbonyl represents an amino acid residue;

$R^2$ together with the carbon to which it is attached and the alpha-nitrogen and alpha-carbonyl represents an amino acid residue;

X represents a bond or an amino acid residue;

$R^3$ represents H, —$(CH_2)_n$—$NR^6R^7$, or $C_{1-6}$ alkyl;

$R^4$ represents H, $C_{1-6}$alkyl, —$(CH_2)_n NR^6R^7$, —$R^A$-L-$Ar^1$, or $R^3$ together with $R^4$ and the nitrogen to which they are attached form a 5 or 6 membered heterocyclic group optionally including a further heteroatom selected from N, O or S, wherein said heterocyclic group, such as piperazine, is optionally substituted by one or two groups independently selected from:
$C_{1-4}$ alkyl,
$C_{5-7}$ cycloalkyl,
pyridinyl,
—$(CH_2)_m NR^8R^9$,
piperidinyl optionally substituted by $C_{1-4}$alkyl, for example substituted on nitrogen;
benzyl optionally substituted on the ring with 1 or 2 substituents independently selected from chloro, bromo, nitro, $C_{1-4}$ alkyl and $C_{1-4}$ alkoxy;
$YAr^1$;

$R^A$ represents a bond, —$C_{0-9}$alkyl$C_{6-10}$aryl, —$C_{0-9}$alkyl$C_{5-11}$heteroaryl, —$C_{1-9}$heteroalkyl$C_{5-11}$heteroaryl —$C_{0-9}$alkyl$C_{3-6}$cycloalkyl, —$C_{1-9}$heteroalkyl$C_{5-11}$heterocyclic or —$C_{0-9}$alkyl$C_{5-11}$heterocycle;

L represents a straight or branched $C_{0-15}$alkyl chain wherein optionally one or more carbons are replaced by a heteroatom independently selected from N, O and S, wherein said chain is optionally substituted by one or more, oxo or nitro groups with the proviso that a heteroatom is not bonded directly to the N of the group —$NR^3R^4$;

Y represents a straight or branched $C_{0-15}$alkyl chain wherein optionally one or more carbons are replaced by a heteroatom independently selected from N, O and S, wherein said chain is optionally substituted by one or more (e.g. 1 or 2), oxo or nitro groups;

$Ar^1$ represents phenyl substituted by one or two $NO_2$ groups or one to five, such as 2, 3, or 4, halogen groups, or one or two $C_{1-3}$haloalkyl groups, or a combination thereof;

$R^5$ together with the carbon to which it is attached and the alpha-nitrogen and alpha-carbonyl represents an amino acid residue:

$R^6$ represents H or $C_{1-6}$alkyl;
$R^7$ represents H or $C_{1-6}$alkyl;

$R^6$ together with $R^7$ and the nitrogen to which they are attached form a 5 or 6 membered heterocyclic group optionally including a further heteroatom selected from N, O and S, wherein said heterocyclic group is optionally substituted by one or two groups independently selected from:
$C_{1-4}$alkyl,
$C_{6-7}$cycloalkyl,
pyridinyl,
—$(CH_2)_m NR^8R^9$,
piperidinyl optionally the substituted by $C_{1-4}$alkyl, for example substituted on nitrogen;

benzyl optionally substituted on the ring with 1 or 2 substituents independently selected from chloro, bromo, nitro, $C_{1-4}$alkyl and $C_{1-4}$alkoxy;
$YAr^1$;

$R^8$ represents H or $C_{1-6}$ alkyl;
$R^9$ represents H or $C_{1-6}$ alkyl;
Z represents H, $C_{1-6}$ alkyl, or an amino acid residue;
n represents 2 to 12;
m represents 1 to 8;
p represents 0 or 1; and the fragment:

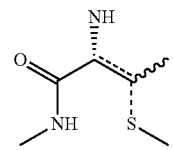

represents:

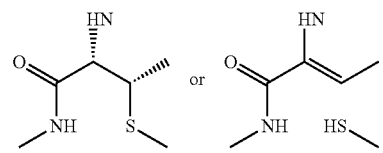

or the E isomer of the latter, or a pharmaceutically acceptable salt thereof.

In one embodiment the compounds employed in the invention are those wherein the amino acid employed in $R^1$, $R^2$ and/or $R^5$ is proteinogenic.

In one embodiment the type B lantibiotic is defined as follows:

$R^1$ together with the carbon to which it is attached and the alpha-nitrogen and alpha-carbonyl represents an amino acid residue;

$R^2$ together with the carbon to which it is attached and the alpha-nitrogen and alpha-carbonyl represents an amino acid residue;

X represents a bond or an amino acid residue;

$R^3$ represents H or $C_{1-6}$alkyl;

$R^4$ represents H, $C_{1-6}$alkyl, —$R^A$-L-$Ar^1$, or $R^3$ together with $R^4$ and the nitrogen to which they are attached form a 5 or 6 membered heterocyclic group optionally including a further heteroatom selected from N, O and S, wherein said heterocyclic group is substituted by $YAr^1$;

$R^A$ represents a bond, —$C_{0-9}$alkyl$C_{6-10}$aryl, —$C_{0-9}$alkyl$C_{5-11}$heteroaryl, —$C_{1-9}$heteroalkyl$C_{5-11}$heteroaryl, —$C_{0-9}$alkyl$C_{3-6}$cycloalkyl, —$C_{1-9}$heteroalkyl$C_{5-11}$heterocyclic or —$C_{0-9}$alkyl$C_{5-11}$ heterocycle;

L represents a straight or branched $C_{0-15}$alkyl chain wherein optionally one or more carbons are replaced by a heteroatom independently selected from N, O and S, wherein said chain is optionally substituted by one or more, oxo or nitro groups with the proviso that a heteroatom is not bonded directly to the N of the group —$NR^3R^4$;

Y represents a straight or branched $C_{0-15}$alkyl chain wherein optionally one or more carbons are replaced by a heteroatom independently selected from N, O and S, wherein said chain is optionally substituted by one or more (e.g. 1 or 2), oxo or nitro groups;

$Ar^1$ represents phenyl substituted by one or two $NO_2$ groups or one to five, such as 2, 3, or 4, halogen groups, or one or two $C_{1-3}$haloalkyl groups, or a combination thereof;

$R^5$ together with the carbon to which it is attached and the alpha-nitrogen and alpha-carbonyl represents an amino acid residue:

Z represents H, $C_{1-6}$alkyl or an amino acid residue;

p represents 0 or 1; and the fragment:

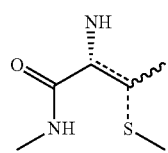

represents:

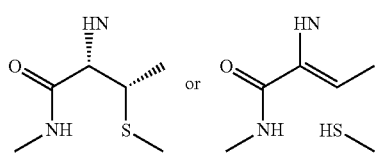

or the E isomer of the latter, or a pharmaceutically acceptable salt thereof.

Paragraph 1. In one embodiment there is provided a compound of formula (I), wherein the fragment:

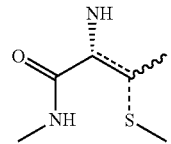

represents:

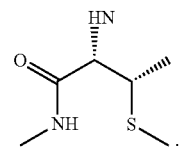

Paragraph 2. In one embodiment there is provided a compound of formula (I) including as defined in paragraph 1, wherein Z is H or Ala.

Paragraph 3. In one embodiment there is provided a compound of formula (I) including as defined in paragraph 1 or 2, wherein Z is H.

Paragraph 4. In one embodiment there is provided a compound of formula (I) including as defined in any one of paragraphs 1 to 3, wherein $Ar^1$ represents phenyl substituted by one or two $NO_2$ groups or one to five, such as 2, 3, or 4, halogen groups, or a combination thereof.

Paragraph 5. In one embodiment there is provided a compound of formula (I) including as defined in any one of claims 1 to 4, wherein the compound is of formula (II):

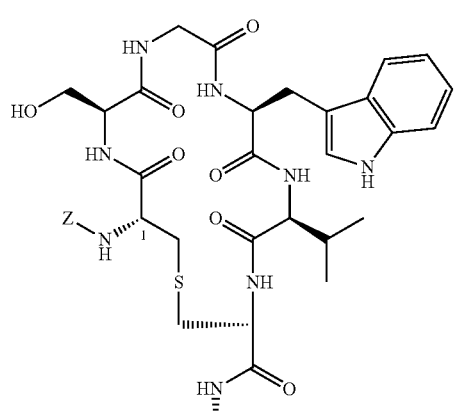

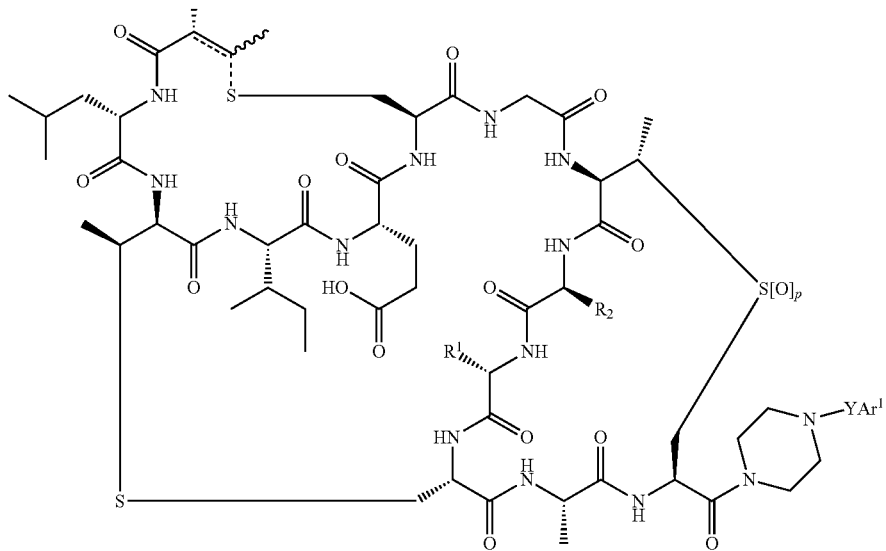

wherein Z, R¹, R², p, YAr¹ and p are as defined above for compounds of formula (I).

Paragraph 6. In one embodiment there is provided a compound of formula (I) including as defined in any one of paragraphs 1 to 5 wherein Y is $C_0$.

Paragraph 7. In one embodiment there is provided a compound of formula (I) including as defined in any one of paragraphs 1 to 5 wherein Y is —$CH_2$—.

Paragraph 8. In one embodiment there is provided a compound of formula (I) including as defined in any one of paragraphs 1 to 5, wherein Y is a $C_{2-12}$alkyl chain wherein optionally one or more carbons (for example 1, 2 or 3) are replaced by a heteroatom independently selected from N, O and S, and said chain is optionally substituted by one or more (for example 1 or 2), oxo or nitro groups.

Paragraph 8. In one embodiment there is provided a compound of formula (I) including as defined in paragraph 7, wherein Y is —$CH_2CH_2NHC(O)$—, —$CH_2CH_2CH_2NHC(O)$— or —$CH_2CH_2NHCH_2$—.

Paragraph 9. In one embodiment there is provided a compound of formula (I) including as defined in any one of claims 1 to 4 wherein the compound is of formula (III):

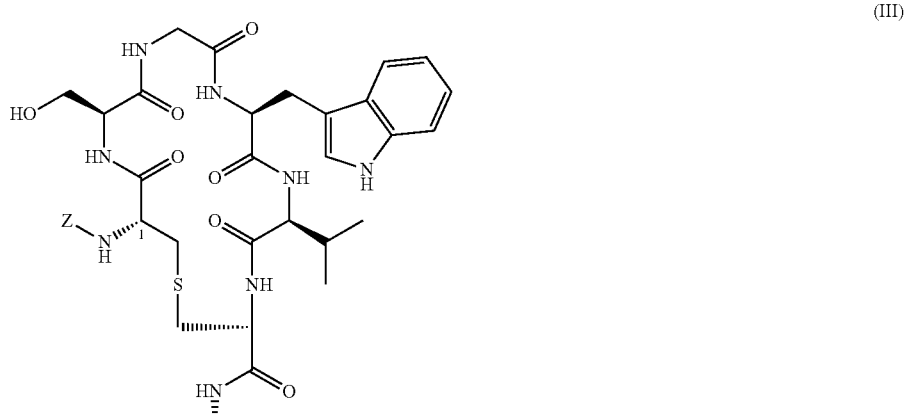

(III)

-continued

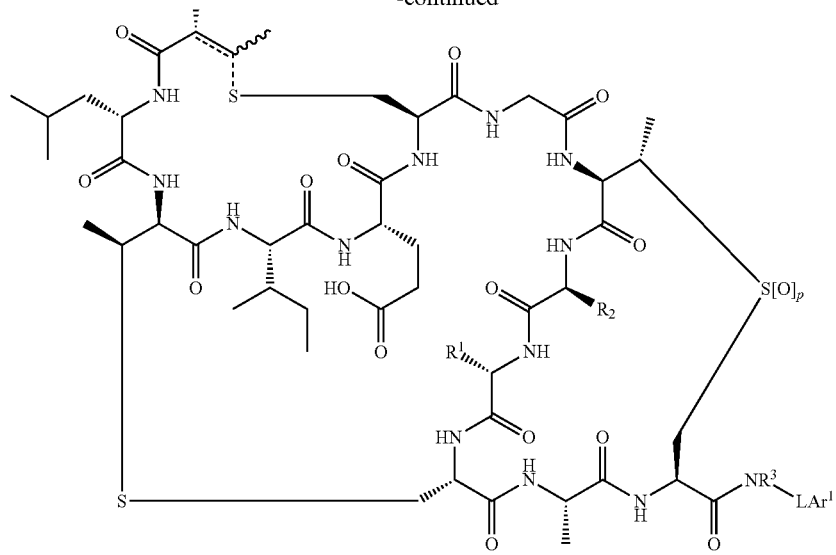

wherein $R^1$, $R^2$, $R^3$, p, Z, L and $Ar^1$ are defined above for compounds of formula (I).

Paragraph 10. In one embodiment there is provided a compound of formula (I) including as defined in any one of claims 1 to 9, wherein $R^3$ is H.

Paragraph 11. In one embodiment there is provided a compound of formula (I) including as defined in any one of claims 1 to 10, wherein $Ar^1$ is di-nitrophenyl or di-halophenyl.

Paragraph 12. In one embodiment there is provided a compound of formula (I) including as defined in paragraph 11, wherein $Ar^1$ is selected from 3,5-di-chlorophenyl, 3,4-di-chlorophenyl, 2,4-di-chlorophenyl, 3,5-di-fluorophenyl, 3,4-di-fluorophenyl or 2,4-di-fluorophenyl.

Paragraph 13. In one embodiment there is provided a compound of formula (I) including as defined in claim 11, wherein $Ar^1$ is selected from 3,5-di-nitrophenyl, 3,4-di-nitrophenyl or 2,4-di-nitrophenyl.

Paragraph 14. In one embodiment there is provided a compound of formula (I) including as defined in any one of paragraphs 1 to 4 and 10 to 13, wherein L represents $C_0$.

Paragraph 15. In one embodiment there is provided a compound of formula (I) including as defined in any one of claims 1 to 4 and 10 to 13, wherein L represents a straight or branched $C_{1-9}$ alkyl chain wherein optionally one or more, such as one, carbon(s) is/are replaced by a heteroatom selected from O, N and S.

Paragraph 16. In one embodiment there is provided a compound of formula (I) including as defined in paragraph 15, wherein L is a straight alkyl chain.

Paragraph 17. In one embodiment there is provided a compound of formula (I) including as defined in to any one of paragraph 10 to 13 and 16, wherein L is $CH_2$.

Paragraph 18. In one embodiment there is provide a compound of formula (I) including as defined in any one of paragraphs 1 to 4 and 10 to 13, wherein L represents —$(CH_2)_i$NH$(CH_2)_j$; wherein i is an integer 1 to 12, j is 0 or 1.

Paragraph 19. In one embodiment there is provided a compound of formula (I) including as defined in paragraph 18 selected from —$(CH_2)_2NHCH_2$—, —$(CH_2)_3NHCH_2$—, —$(CH_2)_4NHCH_2$—, —$(CH_2)_5NHCH_2$—, —$(CH_2)_6NHCH_2$—, —$(CH_2)_7NHCH_2$— and —$(CH_2)_8NHCH_2$—.

Paragraph 20. In one embodiment there is provided a compound of formula (I) as defined in any one of paragraphs 1 to 4 and 10 to 13, wherein L represents a straight $C_{1-15}$alkyl chain wherein optionally one or two carbons are replaced by a heteroatom independently selected from N, O and S, and said chain is optionally substituted by one or two, oxo groups.

Paragraph 21. In one embodiment there is provided a compound of formula (I) including as defined in paragraph 20 selected from —$(CH_2)_3NHCO$—, —$(CH_2)_3NH(CH_2)_3NHCH_2$— and —$(CH_2)_7NHSO_2$—.

Paragraph 22. In one embodiment there is provided a compound of formula (I) including as defined in any one of paragraphs 1 to 21, wherein $R^1$ represents Val or Ile.

Paragraph 23. In one embodiment there is provided a compound of formula (I) including as defined in any one of paragraphs 1 to 22, wherein $R^2$ represents Leu or Val.

Paragraph 24. In one embodiment there is provided a compound selected from the comprising or consisting of:

Deoxyactagardine B (3,5-dichlorobenzylamine)monocarboxamide;
Actagardine (3,5-dichlorobenzylamine)monocarboxamide;
Deoxyactagardine B 19-[4-(4'-nitrophenyl)piperazine]monocarboxamide;
Deoxyactagardine B 19-[4-(4'-chlorophenyl)piperazine]monocarboxamide;
Deoxyactagardine B [2,4-dichlorobenzylamine]monocarboxamide;
Deoxyactagardine B [4-(3',5'-dichlorobenzyl)piperazine]monocarboxamide;
Deoxyactagardine B [4-(2'-fluoro-4'-bromobenzyl)-piperazine]monocarboxamide;
Deoxyactagardine B [4-(4'-nitrobenzyl)piperazine]monocarboxamide;
Deoxyactagardine B [4-bromobenzylamine]monocarboxamide;
Deoxyactagardine B [4-(3',4'-dichlorophenyl)piperazine]monocarboxamide;
Deoxyactagardine B [3-(3',5'-dichlorobenzylamino)-1-propylamine]monocarboxamide;
Deoxyactagardine B [7-(3',5'-dichlorobenzylamino)-1-heptylamine]monocarboxamide;
Deoxyactagardine B [4-(2'-(3'',5''-dichlorobenzylamino)ethyl)-piperazine]monocarboxamide;

Deoxyactagardine B [1-(4-chlorophenyl)piperazine]monocarboxamide;
Deoxyactagardine B (2,4-difluorobenzylamine)monocarboxamide;
Deoxyactagardine B 19-[4-(2'-(3",5"-dinitrobenzamido)-ethyl)-piperazine]monocarboxamide;
V15F Actagardine (3,5-dichlorobenzylamine)monocarboxamide;
Deoxyactagardine B [3-(3',5'-dichlorobenzamido)-propylamine]monocarboxamide;
Deoxyactagardine B 19-[4-(3',5'-dichlorobenzylaminomethyl)-benzyl]monocarboxamide;
Deoxyactagardine B [3-(3'-(3",5"-dichlorobenzylamino)-propylamino)propylamine]monocarboxamide;
Deoxyactagardine B (2,5-dichlorobenzylamine)monocarboxamide;
Deoxyactagardine B (3,4-dichlorobenzylamine)monocarboxamide;
Deoxyactagardine B (2-chlorobenzylamine)monocarboxamide;
Deoxyactagardine B (3-chlorobenzylamine)monocarboxamide;
Deoxyactagardine B (4-chlorobenzylamine)monocarboxamide;
Deoxyactagardine B (2,6-dichlorobenzylamine)monocarboxamide;
Deoxyactagardine B [6-(2',4',6'-trichlorobenzenesulfonamido)-hexylamine]monocarboxamide;
Deoxyactagardine B [5-(3',5'-dichlorobenzylamino)-pentylamine]monocarboxamide;
Deoxyactagardine B [2-(3',5'-dichlorobenzylamino)ethylamine]monocarboxamide;
Deoxyactagardine B [6-(3',5'-dichlorobenzylamino)-hexylamine]monocarboxamide
Deoxyactagardine B [8-(3',5'-dichlorobenzylamino)-octylamine]monocarboxamide.
Deoxyactagardine B [3-(2'-aminomethyl-4'-(2",4"-dichlorophenyl)-furanyl)propylamine]monocarboxamide;
Deoxyactagardine B [3-(2'-aminomethyl-4'-(2"-nitro-4"-chlorophenyl)-furanyl)propylamine]monocarboxamide;
Deoxyactagardine B [3-(2'-aminomethyl-4'-(2",4"-dichlorophenyl)-furanyl)propylamine]monocarboxamide; and
Deoxyactagardine B [3-(2'-aminomethyl-4'-(2"-nitro-4"-chlorophenyl)-furanyl)propylamine]monocarboxamide.

Paragraph 25. In one embodiment there is provided a compound of the formula (IV):

wherein:
—X1-X2- represents -Leu-Val-;
—Y— is —S—;
Z is either an amino acid or —NH$_2$ wherein the latter represents the N-terminus of the Ala at position 1;
R represents —OH or —NR$^3$R$^4$, wherein R$^3$ and R$^4$ independently represent:
(i) hydrogen;
(ii) a group of formula —(CH$_2$)$_n$—NR$^6$R$^7$, in which n represents an integer from 2 to 8 and R$^6$ and R$^7$ independently represent hydrogen or C$_{1-4}$alkyl, or R$^6$ and R$^7$ taken together represents a group —(CH$_2$)$_3$—, —(CH$_2$)$_4$—, (CH$_2$)$_2$—O—(CH$_2$)$_2$—, —(CH$_2$)$_2$—S—(CH$_2$)$_2$ or —(CH$_2$)$_5$—; or
R$^3$ and R$^4$ taken together with the adjacent nitrogen atom represent a piperazine moiety which may be substituted at position 4 with a substituent selected from:
(a) C$_{1-4}$alkyl;
(b) C$_{5-7}$cycloalkyl;
(c) pyridyl,
(d) —(CH$_2$)$_n$—NR$^6$R$^7$ in which p represents an integer from 1 to 8 and R$^5$ and R$^6$ independently represent hydrogen or C$_{1-4}$alkyl;
(e) piperidinyl;
(f) substitute piperidinyl, wherein the substituted piperindinyl bears a N-substitutent which is C$_{1-4}$alkyl;
(g) benzyl; and
(h) substituted benzyl, wherein the phenyl moiety bears 1 or 2 substituents selected from chloro, bromo, nitro, C$_{1-4}$alkyl and C$_{1-4}$alkoxy,
or a pharmaceutically acceptable salt thereof.

Paragraph 26. In one embodiment there is provided a compound of formula (IV) including as defined in paragraph 25, wherein Z is an amino acid.

Paragraph 27. In one embodiment there is provided a compound of formula (IV) including as defined in paragraph 26, wherein the amino acid is Ala.

Paragraph 28. In one embodiment there is provided a compound of formula (IV) including as defined in paragraph 25, wherein Z is —NH$_2$ Paragraph 29. In one embodiment there is provided a compound of formula (IV) including as defined in any one of paragraphs 25 to 28, wherein R is OH.

Paragraph 30. In one embodiment there is provided a compound of formula (IV), including as defined in any one of paragraphs 25 to 28, wherein R$^1$ and R$^2$ independently represent:

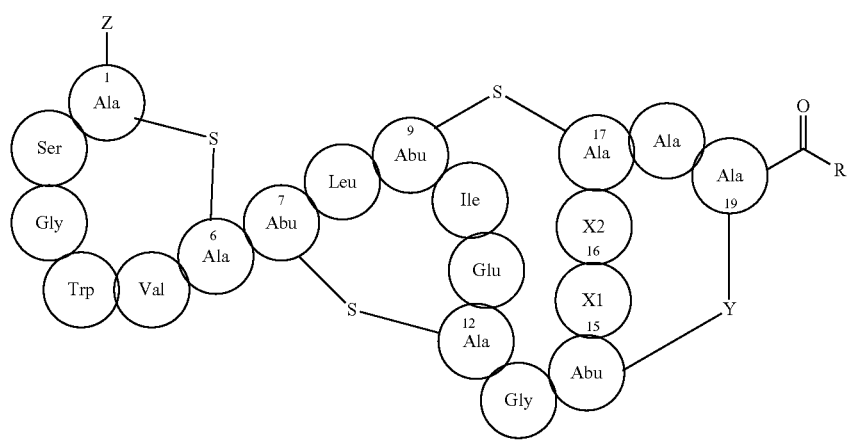

(IV)

(i) hydrogen;
(ii) a group of formula —$(CH_2)_n$—$NR^6R^7$, in which n represents an integer from 2 to 8 and $R^3$ and $R^4$ independently represent hydrogen or $C_{1-4}$alkyl.

Paragraph 31. In one embodiment there is provided a compound of formula (IV), wherein the compound is selected from the group consisting of:
deoxyactagardine B N-[3-dimethylaminopropyl]monocarboxamide;
deoxyactagardine B N-[1-(1-methyl-4-piperidinyl)piperazine]monocarboxamide;
deoxyactagardine B [1-(3-dimethylaminopropyl)piperazine]monocarboxamide;
deoxyactagardine B;
D-Ala(0)deoxyactagardine B;
L-Ile(0)deoxyactagardine B;
L-Val(0)deoxyactagardine B;
L-Phe(0)deoxyactagardine B;
L-Lys(0)deoxyactagardine B; and
L-Trp(0)deoxyactagardine B.

In one embodiment there is provided a compound of formula (IA)

wherein
A together with the carbon to which it is attached and the alpha-nitrogen and alpha-carbonyl represents an amino acid residue;
B together with the carbon to which it is attached and the alpha-nitrogen and alpha-carbonyl represents an amino acid residue;
X is —$NH(CH_2)_pNH_2$;
Z represents H, $C_{1-6}$ alkyl, or an amino acid residue; and pharmaceutically acceptable salts, hydrates and solvates thereof, in particular
Deoxyactagardine B (7-amino-1-heptylamide monocarboxamide);
Deoxyactagardine B [7-(t-butoxycarbonylamido)-1-heptylamide monocarboxamide];
Deoxyactagardine B (2-amino-1-ethylamide monocarboxamide)
Deoxyactagardine B (3-amino-1-propylamide monocarboxamide);
Deoxyactagardine B (5-amino-1-pentylamide monocarboxamide);

(IA)

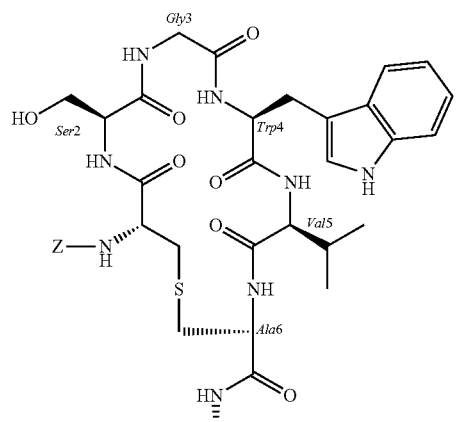

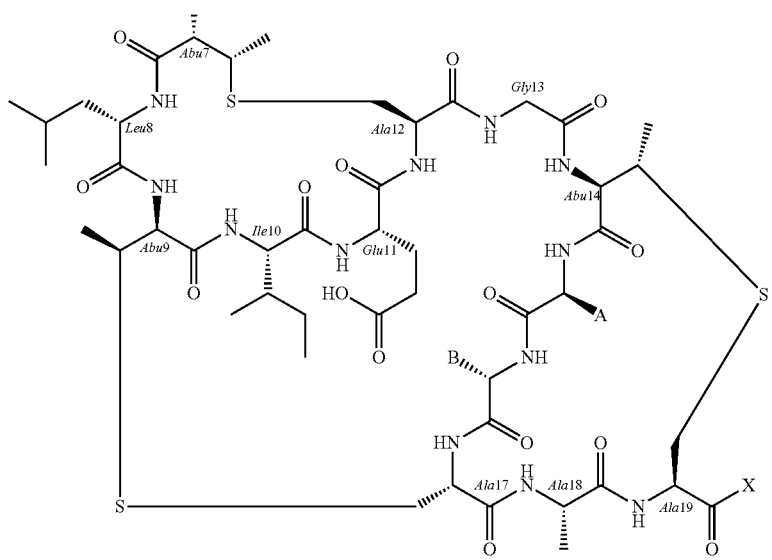

Deoxyactagardine B (9-amino-1-nonylamide monocarboxamide);
Deoxyactagardine B (12-amino-1-dodecylamide monocarboxamide).

In one embodiment there is provided a compound of formula (IB):

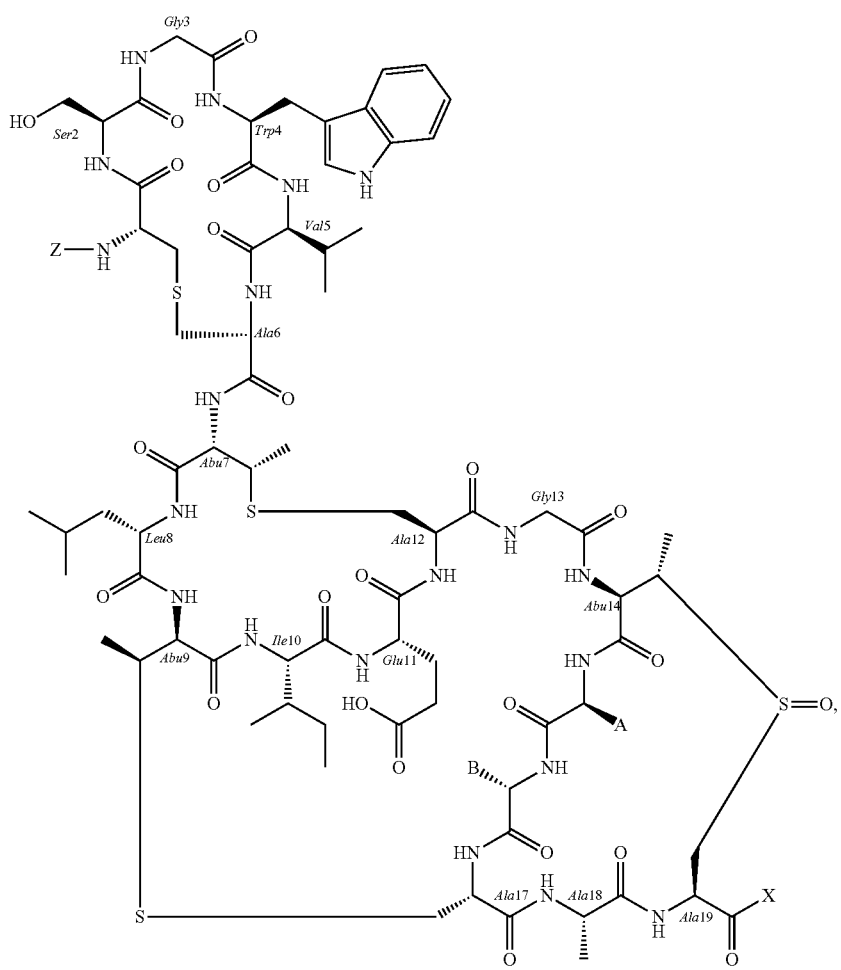

(IB)

wherein
- A together with the carbon to which it is attached and the alpha-nitrogen and alpha-carbonyl represents an amino acid residue;
- B together with the carbon to which it is attached and the alpha-nitrogen and alpha-carbonyl represents an amino acid residue;
- X is —NH(CH$_2$)$_p$NH$_2$;
- Z represents H, C$_{1-6}$ alkyl, an amino acid residue; and pharmaceutically acceptable salts, hydrates and solvates thereof, in particular actagardine (7-amino-1-heptylamide monocarboxamide);

Actagardine 1,3-diaminopropane monocarboxamide; and
Actagardine 1,4-diaminobutane monocarboxamide.

In one embodiment in compounds employed in the present invention A and/or B is a proteinogenic amino acid.

In one embodiment there is provided an aqueous concentrate, suitable for dilution to form an isotonic formulation for infusion according to the present invention, said concentrate comprising:

a salt of a type B lantibiotic;
optionally a sugar alcohol such as glycerol, and/or a saccharide; and
optionally a buffer,
wherein said concentrate can be filtered through a 0.2 μm filter.

In one embodiment the concentrate is colloidal.

In one embodiment the colloidal formulation or concentrate thereof comprises a phase of particulates or sols, for example having an average particle size less than 200 nm.

In one embodiment the concentrate contains all the excipients and lantibiotic of the final formulation for infusion and therefore simply requires dilution with water for injection.

In one embodiment the concentrate does not contain certain excipients, such as sugars and/or glycerol which, for example may be employed ultimately to render the final formulation isotonic. In this embodiment the concentrate will generally be diluted with a sterile isotonic carrier containing the sugar alcohol/saccharide, as appropriate (in particular as described herein).

The concentrate can be prepared in the first instance under non-aseptic conditions by weighing the ingredients including the type B lantibiotic into an appropriate manufacturing vessel. The appropriate amounts of aqueous solutions of glucose, mannitol or sorbitol or alternatively water may then be added to the dry ingredients (or vice versa the dry ingredients may be added to water or an aqueous solution) and the resultant melange mixed until a homogenous liquid composition is obtained.

Care may be required if a high shear mixer is employed because the lantibiotic B is a peptide and may be denatured if subjected to excessive high-speed stirring.

This liquid concentrate of a diluted version thereof may be filtered through a 0.2 μm membrane filter to render it substantially free of pathogens.

In one embodiment the liquid concentrate formulations of the present invention are free or substantially free of visible particulates.

This liquid composition may be filled into suitable vials for storage as liquid concentrate or may be filled into vials for lyophillisation.

Lyophilisation, as employed herein, refers to a dehydration process typically used to preserve a perishable material.

In one embodiment a liquid pharmaceutical formulation or a liquid concentrate, as defined herein, comprising the lantibiotic is lyophilised for storage and reconstituted prior to use with sterile water or an isotonic solution such as glucose, mannitol, sorbitol or a combination thereof to ultimately provide an isotonic formulation for parenteral administration to a patient.

Ultimately provide as employed supra is intended to refer to the fact that the reconstitution may be performed in two steps, for example a step to provide a liquid concentrate and a second step to dilute the concentrate to a final formulation.

A dry formulation in lyophilised from will comprise the type B lantibiotic or a salt thereof (such as salt) and one or more components of the formulation. This dry formulation must be reconstituted to provide a liquid concentrate.

A liquid concentrate will generally require dilution to provide an isotonic formulation suitable for parenteral administration.

In another embodiment a pharmaceutical formulation of a liquid concentrate (such as an infusion concentrate or an injection concentrate), as defined herein, contains the majority of the solid ingredients, save one or more isotonicitinsing agents, and is lyophilised, for storage. The dried formulation is then reconstituted with a sterile isotonic aqueous solution, such as a sugar alcohol solution and/or a saccharide solution and then optionally diluted to provide a formulation suitable for infusion with said isotonic solution.

In one embodiment the liquid concentrate is an infusion concentrate.

Infusion concentrate as employed herein is intended to refer to a liquid concentrate that when diluted provides an isotonic formulation suitable for infusion, for example where in the type B lantibiotic is in the range 5-15 mg/mL, such as 10 mg/mL.

In one embodiment the liquid concentrate is an injection concentrate.

Injection concentrate as employed herein is intended to refer to a liquid concentrate that when diluted provides an isotonic formulation for injection, for example wherein the type B lantibiotic is in the concentration range 10-25 mg/mL, such as 20 mg/mL.

In another embodiment a liquid colloidal pharmaceutical formulation containing all the final mass of the excipients and the lantibiotic is lyophilised for storage and reconstituted with sterile water such that the lantibiotic concentration is about 20 mg/mL and used for dosing by infusion or direct injection.

The present disclosure also provides a method or process for preparing a final formulation described herein from the original components.

The present disclosure provides a method or process for preparing a liquid concentrate from the orginal components.

The present disclosure provides a process of preparing a lyophilised formulation from a final liquid formulation or from a liquid concentrate.

The present disclosure provides a process for reconstituting a lyophilised formulation to provide a final liquid formulation or a liquid concentrate.

The present disclosure provides a process of dilluting a liquid concentrate to provide a final formulation.

In one embodiment a liquid formulation for direct injection according to the disclosure is prepared, by reconstituting a lyophillised formulation to the required volume with water for injection or an isotonic solution (for example reconstituting to a concentration in the range 20-50 mg/mL) and optionally diluting to the same to the required final concentration such as about 20 mg/mL.

In one embodiment a lyophillised formulation according to the present disclosure is reconstituted to provide a concentrate formulation, for example at a concentration of lantibiotic in the range 40-75 mg/mL, such as 50 mg/mL. This concentrate is then diluted to the appropriate level to provide a final formulation for infusion, for example to provide a lantibiotic concentration in the range 1-20 mg/mL for example 1-10 mg/mL.

In one embodiment a liquid formulation for infusion according to the disclosure is provided fully formulated in a bag for infusion, for example an infusion bag suitable for holding 100 mL or 500 mL of formulation, such as 200 to 300 mL.

In one embodiment a liquid formulation for injection is provided fully formulated in a vial for injection.

Fully formulated as employed herein is intended to refer to a final formulation which is suitable for administration to a patient with any further preparative steps by a health care professional.

The final formulation may be manufactured under non-aseptic conditions by weighing the ingredients including the type B lantibiotic or a salt thereof into an appropriate manufacturing vessel. The appropriate amounts of aqueous components or water may then be added and the resultant melange mixed until a homogenous composition is obtained.

Care may be required if a high shear mixer is employed because the lantibiotic B is a peptide and may be denatured if subjected to excessive high-speed stirring.

This composition may be filtered through a 0.2 μm membrane filter to render it substantially free of pathogens.

The final formulation may then be filled into infusion bags and sealed for storage and distribution.

In one embodiment there is provided a method for preparing a sterile formulation for infusion, direct injection or a liquid concentrate, according to the present disclosure, the method comprising the step of filtering the formulation or the components thereof through a 0.2 μm filter.

In one embodiment the formulation according to the disclosure is prepared under aseptic manufacturing conditions.

In one embodiment a formulation according to the disclosure is prepared under non-aseptic manufacturing conditions and filtered to provide a sterile liquid formulation or a liquid concentrate suitable for human or animal use.

Thus the final formulation or liquid concentrate is provided as a sterile formulation. When the final formulation or the liquid concentrate is lyophilised then lyophilisation will be performed after sterilisation.

In one embodiment the formulation and/or concentrate thereof described herein is a colloidal dispersion, for example a colloidal suspension.

In one embodiment a method is provided comprising the step of lyophillising a formulation of the disclosure to provide a formulation in dry form. This may be advantageous from a storage and stability perspective.

In one embodiment an infusion concentrate, as described herein is lyophillised to provide a formulation for reconstitution, for example one dose of the lyophillised formulation is provided in a vial such as a silicone coated vial.

The formulations, in particular liquid formulations, according to the present disclosure may require storage at 4° C. or less.

For parenteral administration to humans, the daily dosage may be in single or divided doses. For systemic administration the daily dose as employed for adult human treatment will range from 2-100 mg/Kg body weight, for example 5-60 mg/Kg body weight, which may be administered in 1 to 4 daily doses, for example, depending on the specific administration and the condition of the patient.

In one embodiment each dose is in the range 1-2,500 mg, for example 100-1,000 mg. The duration of treatment will be dictated by the rate of response rather than by arbitrary numbers of days.

In one embodiment the treatment regime is continued for 1, 2, 3, 4, 5, 6, 7, 8, 9, 10, 11, 12, 13, 14, 15, 16, 17, 18, 19, 20, 21 or more days.

In one embodiment the dose is administered by continuous infusion.

In one embodiment the formulations described herein are provided for use in therapy, for example in the treatment of prophylaxis of gram positive infections, in particular by infusion or direct injection.

Certain compounds employed in the formulations of the present disclosure are believed to have broad anti-microbial activity against gram positive bacteria.

In one aspect, the disclosure provides a formulation as described in any embodiment herein for use in therapy, for example, for treatment of microbial infections such as bacteraemia, endocarditis, pneumonia and microbial infection of soft tissue including surgical wounds, in particular staphylococcal infections including MRSA infection.

In one embodiment a formulation according to the present disclosure is useful for the treatment of enterococcal infections including *E. faecalis* and *E. faecium* infection, for example skin and skin structure infections, endocarditis, urinary tract infection and sepsis.

In one embodiment a formulation according to the present disclosure is useful for the treatment of *S. pyogenes*, for example skin infections such as impetigo, erysipelas and cellulitis, throat infections, scarlet fever, and acute glomerulonephritis.

In one embodiment a formulation according to the present disclosure is useful in the treatment of *Streptococcus pneumoniae* infection, for example pnuemonia, acute sinusitis, otitis media, meningitis, bacteremia, osteomylitis, septic arthritis and endocarditis.

In one aspect there is provided use of an isotonic saccharide and/or sugar alcohols solution or water for injection for dilution of an infusion contrate or lyophillised formulation as described herein.

In one aspect there is provided a use of a saccharide or sugar alcohol for the formulation of a compound or compounds disclosed herein, for infusion (including an infusion concentrate and/or lyophillised version thereof), in particular for the preparation of a parenteral formulation.

In one embodiment there is provided a liquid concentrate according to the disclosure herein for use in treatment, for example in treatment of bacterial infection, such as infection by *Staphylococcus aureus*, in particular, wherein the *Staphylococcus aureus* is methicillin resistant.

Also provided is a method of treating a patient comprising administering a therapeutically effective amount of a formulation as defined herein, for example wherein the treatment is for bacterial infection (as described above), such as infection by *Staphylococcus aureus*, in particular, wherein the *Staphylococcus aureus* is methicillin resistant.

There is also provided a use of a formulation according to disclosure for use in the manufacture of a medicament for treatment or prophylaxis, for example as described supra.

Comprising in the context of the present invention means including.

Described above are embodiments comprising certain integers. Embodiments of the invention described above can be combined as technically appropriate. The present disclosure also extends to corresponding embodiments consisting of said integers as herein described.

EXAMPLES

In each of the compounds below the entity shown is linked to the DAB or actagardine entity through the C terminus and therefore the specific substituents shown correspond to $XNR^3R^4$ in compounds of formula (I).

Compound 1

Deoxyactagardine B
(3,5-dichlorobenzylamine)monocarboxamide

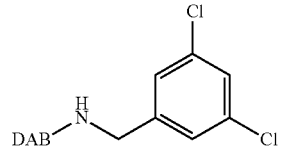

Deoxyactagardine B [DAB] (200 mg), 3,5-dichlorobenzylamine (38 mg) and diisopropylethylamine (35 µL) were dissolved in dry dimethylformamide (1 mL). A solution of benzotriazole-1-yl-oxy-tris-pyrrolidino-phosphonium hexafluorophosphate (PyBOP) (84 mg) in dry DMF (2 mL) was added portionwise. The reaction was followed by analytical HPLC (See Table 1) and PyBOP was added until the starting material had been consumed.

TABLE 1

Analytical HPLC conditions for the separation of lantibiotic (e.g. actagardine, actagardine B, or deoxy-actagardine B) and diaminoalkane derivatised products.

| | | | |
|---|---|---|---|
| Column: | Zorbax 5µ C18(2) 150 × 4.6 mm | | |
| Mobile Phase A: | 30% Acetonitrile in 20 mM potassium phosphate buffer pH 7.0 | | |
| Mobile Phase B: | 65% Acetonitrile in 20 mM potassium phosphate buffer pH 7.0 | | |
| Flow rate: | 1 mL/min | | |
| Gradient: | Time 0 min | 100% A | 0% B |
| | Time 10 min | 0% A | 100% B |
| | Time 11 min | 0% A | 100% B |
| | Time 11.2 min | 100% A | 0% B |
| | Cycle time 15 min | | |

TABLE 1-continued

Analytical HPLC conditions for the separation of lantibiotic
(e.g. actagardine, actagardine B, or deoxy-actagardine B)
and diaminoalkane derivatised products.

| | |
|---|---|
| Injection volume: | 10 μL |
| Detection: | 210 nm |

The crude reaction mixture was poured into 30% aqueous methanol and the resulting solution was loaded on to a Varian Bond Elut C18 column (30 g). The column was then washed sequentially with 50%, 60%, 70%, 80%, 90% aqueous methanol, with most of the desired material eluting in the 70% fraction. Column chromatography on silica gel (eluent dichloromethane:ethanol:ammonia 10:8:1) gave material of >90% purity by U.V. at 210 nm. Yield 107 mg (50%). Mass calculated for $(M+2H)^{+2}$ 1015.5, found 1015.57. Calculated for $[M+H+Na]^{+2}$ 1026, found 1025.32.

Samples were analysed by LC-MS using the conditions described in Table 2.

TABLE 2

LC/MS conditions for the analysis of lantibiotic
(e.g. deoxy-actagardine B) and derivatised products.

| | | | |
|---|---|---|---|
| Column: | Zorbax 5μ C18(2) 150 × 4.6 mm | | |
| Mobile Phase A: | 10% acetonitrile, 0.1% formic acid | | |
| Mobile Phase B: | 90% acetonitrile, 0.1% formic acid | | |
| Flow rate: | 1 mL/min | | |
| Gradient: | Time 0 min | 100% A | 0% B |
| | Time 10 min | 0% A | 100% B |
| | Time 11 min | 0% A | 100% B |
| | Time 11.1 min | 100% A | 0% B |
| | Cycle time 15 min | | |
| Injection volume: | 20 μL | | |
| Mass Spectrometer parameters | | | |
| Ionisation | Electrospray +ve | | |
| Mass range | 250-1500 mu | | |
| Capillary voltage | 3.10 KV | | |
| Cone voltage | 40 V | | |
| Skimmer lens offset | 5 V | | |
| Ion energy | 1.4 V | | |

Compound 2

Actagardine
(3,5-dichlorobenzylamine)monocarboxamide

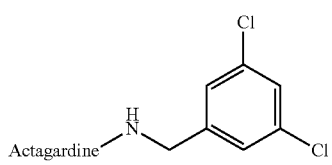

Actagardine (3,5-dichlorobenzylamine)monocarboxamide was prepared from actagardine and 3,5-dichlorobenzylamine according to the procedure described for compound 1. Yield 8%. Calculated for $[M+2H]^{+2}$ 1023.5, found 1023.7

Compound 3

Deoxyactagardine B 19-[4-(4'-nitrophenyl)piperazine]monocarboxamide

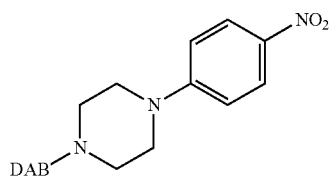

Deoxyactagardine B [4-(4'-nitrophenyl)piperazine]monocarboxamide was prepared from deoxyactagardine B and 4-nitrophenyl-piperazine utilising the procedure described for compound 1. Yield 73%. Calculated for $[M+2H]^{+2}$ 1031.5, found 1031.9.

Example 4

Deoxyactagardine B 19-[4-(4'-chlorophenyl)piperazine]monocarboxamide

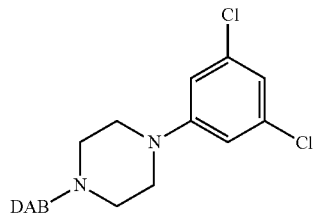

Deoxyactagardine B 19-[4-(4'-chlorophenyl)piperazine]monocarboxamide was prepared from deoxyactagardine B and 4-chlorophenyl-piperazine utilising the procedure described for compound 1. Yield 95%. Calculated for $[M+2H]^{+2}$ 1026.0, found 1026.2.

Compound 5

Deoxyactagardine B
[2,4-dichlorobenzylamine]monocarboxamide

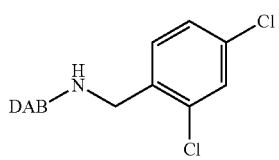

Deoxyactagardine B (2,4-dichlorobenzylamine)monocarboxamide was prepared from deoxyactagardine B and 2,4- dichlorobenzylamine utilising the procedure described for compound 1. Yield 86%. Calculated for [M+2H]$^{+2}$ 1015.5, found 1015.1.

Compound 6

Deoxyactagardine B [4-(3',5'-dichlorobenzyl)piperazine]monocarboxamide

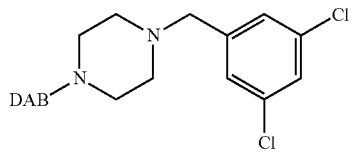

Deoxyactagardine B [4-(3',5'-dichlorobenzyl)piperazine]monocarboxamide was prepared from deoxyactagardine B and 4-(3',5'-dichlorobenzyl)piperazine utilising the procedure described for compound 1. Yield 80%. Calculated for [M+2H]$^{+2}$ 1050.0, found 1050.3.

Compound 7

Deoxyactagardine B[4-(2'-fluoro-4'-bromobenzyl)piperazine]monocarboxamide

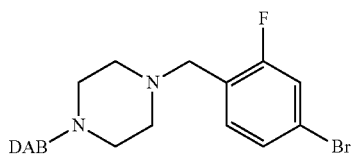

Deoxyactagardine B [4-(2'-fluoro-4'-bromobenzyl)piperazine]monocarboxamide was prepared from deoxyactagardine B and 4-(2'-fluoro-4'-bromobenzyl)piperazine utilising the procedure described for compound 1. Yield 83%. Mass calculated for (M+2H)$^{+2}$ 1064.5, found 1063.7.

Compound 8

Deoxyactagardine B [4-(4'-nitrobenzyl)piperazine]monocarboxamide

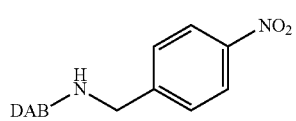

Deoxyactagardine B 19-[4-(4'-nitrobenzyl)piperazine]monocarboxamide was prepared from deoxyactagardine B and 4-(4'-nitrobenzyl)piperazine utilising the procedure described for compound 1. Yield 88%. Mass calculated for (M+2H)$^{+2}$ 1004.0, found 1003.6.

Compound 9

Deoxyactagardine B [4-bromobenzylamine]monocarboxamide

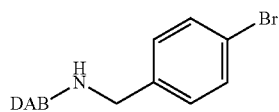

Deoxyactagardine B [4-bromobenzylamine]monocarboxamide was prepared from deoxyactagardine B and 4-bromobenzylamine utilising the procedure described for compound 1. Yield 92%. Mass calculated for (M+2H)$^{+2}$ 1021, found 1022.6.

Compound 10

Deoxyactagardine B [4-(3',4'-dichlorophenyl)piperazine]monocarboxamide

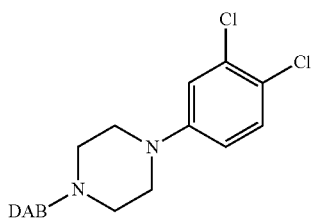

Deoxyactagardine B [4-(3',4'-dichlorophenyl)piperazine]monocarboxamide was prepared from deoxyactagardine B and 4-(3',4'-dichlorophenyl)piperazine utilising the procedure described for compound 1. Yield 33%. Calculated for [M+2H]$^{+2}$ 1043.0, found 1043.5.

Compound 11

Deoxyactagardine B [3-(3',5'-dichlorobenzylamino)-1-propylamine]monocarboxamide

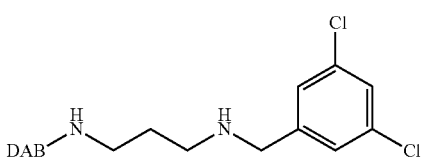

A suspension of sodium borohydride (0.26 g) in dichloromethane was treated with acetic acid (1.6 mL) and stirred for 15 minutes. A solution of N-Boc-1,3-diaminopropane (0.2 g) and 3,5-dichlorobenzaldehyde (0.61 g) in dichloromethane (10 mL) was added and the mixture was stirred at room temperature for 20 h. The mixture was then partitioned between aqueous sodium bicarbonate and ethyl acetate. The organic solution was evaporated and the residue purified by column chromatography on silica gel to yield 3-(3',5'-dichlorobenzylamino)-1N-(t-butoxycarbonyl)-propylamine as a white solid.

The purified product was dissolved in 90% trifluoroacetic acid (4 mL) and stirred for 3 h at room temperature. The trifluoroacetic acid was removed in vacuo and the residue was then partitioned between aqueous sodium bicarbonate and ethyl acetate. The organic extracts were dried (MgSO$_4$) and evaporated to leave N-(3',5'-dichlorobenzyl)-1,3-diaminopropane as a white solid.

To a solution of deoxyactagardine B (1.0 g), N-(3',5'-dichlorobenzyl)-1,3-diaminopropane (0.34 g) and diisopropylethylamine (0.32 mL) in dry dimethylformamide (5 ml) a solution of benzotriazole-1-yl-oxy-tris-pyrrolidino-phosphonium hexafluorophosphate (PyBOP) (0.52 g) in dry dimethylformamide (2 mL) was added in portions until the reaction was complete as measured by analytical HPLC (conditions as in Table 1). The coupling product was purified as described for the compound of compound 1. Yield 33%. Calculated for [M+2H]$^{+2}$ 1043.0, found 1043.49.

Compound 12

Deoxyactagardine B [7-(3',5'-dichlorobenzylamino)-1-heptylamine]monocarboxamide

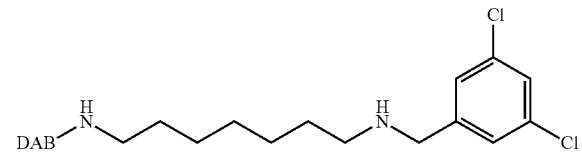

Was prepared from deoxyactagardine B, N-Boc-1,7-diaminoheptane and 3,5-dichlorobenzaldehyde as described for compound 11. Yield 35%. Calculated for [M+2H]$^{+2}$ 1072.0, found 1073.0.

Compound 13

Deoxyactagardine B [4-(2'-(3",5"-dichlorobenzylamino)ethyl)piperazine]monocarboxamide

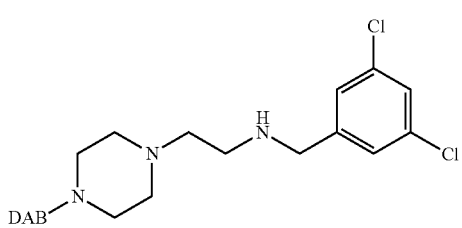

Was prepared from deoxyactagardine B, N-(2-aminoethyl)-piperazine and 3,5-dichlorobenzaldehyde as described for compound 11. Yield 15%. Calculated for [M+2H]$^{+2}$ 1071.5, found 1072.3.

Compound 14

Deoxyactagardine B [1-(4-chlorophenyl)piperazine]monocarboxamide

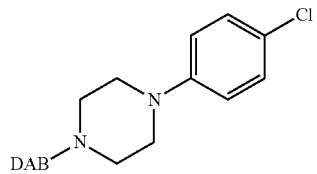

Deoxyactagardine B [1-(4-chlorophenyl)piperazine]monocarboxamide was prepared from deoxyactagardine B and 1-(4-chlorophenyl)piperazine utilising the procedure described for compound 1. Yield 21%. Calculated for [M+H]+2051, found 2052.8.

Compound 15

Deoxyactagardine B (2,4-difluorobenzylamine)monocarboxamide

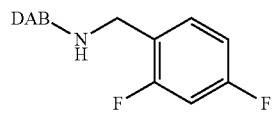

Deoxyactagardine B (2,4-difluorobenzylamine)monocarboxamide was prepared from deoxyactagardine B and 2,4-difluorobenzylamine utilising the procedure described for compound 1. Yield 31%. Calculated for [M+H]+2000.39, found 1999.5.

Compound 16

Deoxyactagardine B 19-[4-(2'-(3",5"-dinitrobenzamido)-ethyl)-piperazine]monocarboxamide

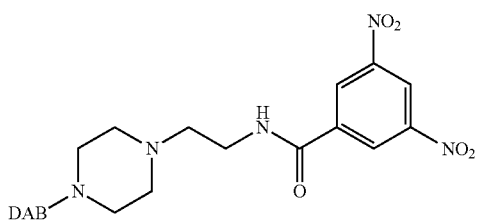

Deoxyactagardine B 19-[4-(2'-(3",5"-dinitrobenzamido)-ethyl)-piperazine]monocarboxamide was prepared from deoxyactagardine B and 4-(2'-(3",5"-dinitrobenzamido)-ethyl)-piperazine utilising the procedure described for compound 1. Yield 20%.

Compound 17

V15F Actagardine (3,5-dichlorobenzylamine)monocarboxamide

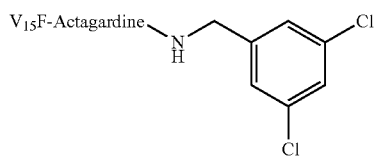

V15F Actagardine (3,5-dichlorobenzylamine)monocarboxamide was prepared from V15F Actagardine and 3,5-dichlorobenzylamine utilising the procedure described for compound 1. Yield 39%. Calculated for $[M+Na\ H]^{+2}$ 1058.5, found 1059. V15F actagardine is where valine 15 in the ring is replaced by phenylalanine.

Compound 18

Deoxyactagardine B [3-(3',5'-dichlorobenzamido)propylamine]monocarboxamide

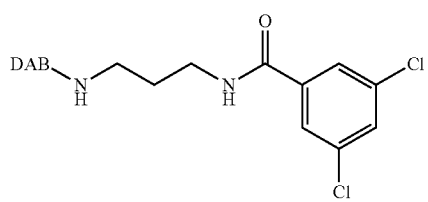

Deoxyactagardine B [3-(3',5'-dichlorobenzamido)-propylamine]monocarboxamide was prepared from deoxyactagardine B and 3-(3',5'-dichlorobenzamido)-propylamine utilising the procedure described for compound 1. Yield 61%. Calculated for $[M+Na+H]^{+2}$ 1062, found 1062.

Compound 19

Deoxyactagardine B [4-(3',5'-dichlorobenzylaminomethyl)benzyl]monocarboxamide

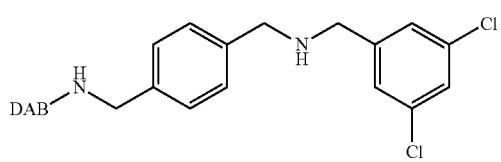

Deoxyactagardine B 19-[4-(3',5'-dichlorobenzylaminomethyl)-benzyl]monocarboxamide was prepared from deoxyactagardine B and 4-(3',5'-dichlorobenzylaminomethyl)-benzylamine utilising the procedure described for compound 1. Yield 37%. Calculated for $[M+2H]^{+2}$ 1075, found 1076.

Compound 20

Deoxyactagardine B [3-(3'-(3",5"-dichlorobenzylamino)propylamino) propylamino]monocarboxamide

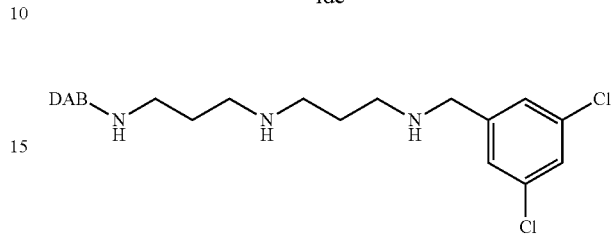

Deoxyactagardine B [3-(3'-(3",5"-dichlorobenzylamino)-propylamino)propylamine]monocarboxamide was prepared from deoxyactagardine B and 3-(3'-(3",5"-dichlorobenzylamino) propylamino)propylamine utilising the procedure described for compound 1. Yield 22%. Calculated for $[M+2H]^{+2}$ 1072.5, found 1073.

Compound 21

Deoxyactagardine B (2,5-dichlorobenzylamine)monocarboxamide

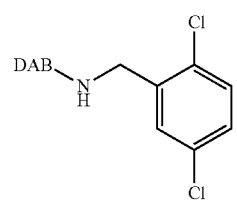

Deoxyactagardine B (2,5-dichlorobenzylamine)monocarboxamide was prepared from deoxyactagardine B and 2,5-dichlorobenzylamine utilising the procedure described for compound 1. Yield 57% Calculated for $[M+Na+H]^{+2}$ 1026.5, found 1026.8.

Compound 22

Deoxyactagardine B (3,4-dichlorobenzylamine)monocarboxamide

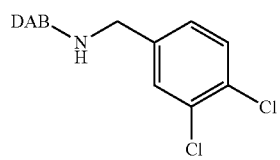

Deoxyactagardine B (3,4-dichlorobenzylamine)monocarboxamide was prepared from deoxyactagardine B and 3,4- dichlorobenzylamine utilising the procedure described for compound 1. Yield 41%. Calculated for [M+Na+H]$^{+2}$ 1026.5, found 1026.2.

Compound 23

Deoxyactagardine B
(2-chlorobenzylamine)monocarboxamide

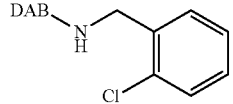

Deoxyactagardine B (2-chlorobenzylamine)monocarboxamide was prepared from deoxyactagardine B and 2-chlorobenzylamine utilising the procedure described for compound 1. Yield 50%. Calculated for [M+Na+H]$^{+2}$ 1009.5, found 1009.6.

Compound 24

Deoxyactagardine B
(3-chlorobenzylamine)monocarboxamide

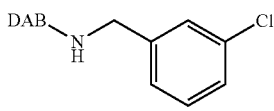

Deoxyactagardine B (3-chlorobenzylamine)monocarboxamide was prepared from deoxyactagardine B and 3-chlorobenzylamine utilising the procedure described for compound 1. Yield 62%. Calculated for [M+Na+H]$^{+2}$ 1009.5, found 1009.4.

Compound 25

Deoxyactagardine B
(4-chlorobenzylamine)monocarboxamide

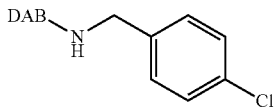

Deoxyactagardine B (4-chlorobenzylamine)monocarboxamide was prepared from deoxyactagardine B and 4-chlorobenzylamine utilising the procedure described for compound 1. Yield 40% Calculated for [M+Na+H]$^{+2}$ 1009.5, found 1009.9.

Compound 26

Deoxyactagardine B
(2,6-dichlorobenzylamine)monocarboxamide

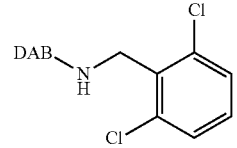

Deoxyactagardine B (2,6-dichlorobenzylamine)monocarboxamide was prepared from deoxyactagardine B and 2,6-dichlorobenzylamine utilising the procedure described for compound 1. Yield 57%. Calculated for [M+Na+H]$^{+2}$ 1026.5, found 1026.2.

Compound 27

Deoxyactagardine B [6-(2',4',6'-trichlorobenzene-sulfonamido)hexylamine]monocarboxamide

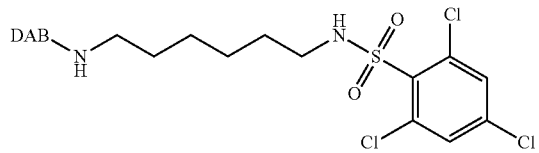

Deoxyactagardine B [6-(2',4',6'-trichlorobenzenesulfonamido)-hexylamine]monocarboxamide was prepared from deoxyactagardine B and 6-(2',4',6'-trichlorobenzenesulfonamido)-hexylamine utilising the procedure described for compound 1. Yield 73%. Calculated for [M+2H]$^{+2}$ 2213, found 2212.8.

Compound 28

Deoxyactagardine B [5-(3',5'-dichlorobenzylamino)-pentylamine]monocarboxamide

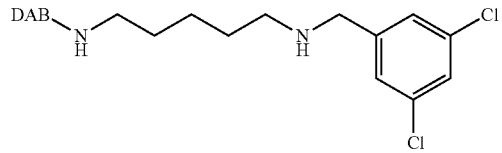

Deoxyactagardine B [5-(3',5'-dichlorobenzylamino)-pentylamine]monocarboxamide was prepared from deoxyactagardine B and 5-(3',5'-dichlorobenzylamino)-pentylamine

Compound 29

Deoxyactagardine B [2-(3',5'-dichlorobenzylamino)ethylamine]monocarboxamide

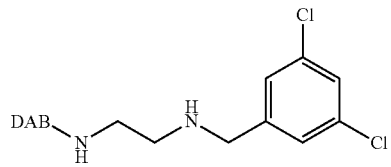

Deoxyactagardine B [2-(3',5'-dichlorobenzylamino)ethylamine]monocarboxamide was prepared from deoxyactagardine B and 2-(3',5'-dichlorobenzylamino)ethylamine utilising the procedure described for compound 1. Yield 51% Calculated for $[M+2H]^{+2}$ 1037.0, found 1038.0.

Compound 30

Deoxyactagardine B [6-(3',5'-dichlorobenzylamino)-hexylamine]monocarboxamide

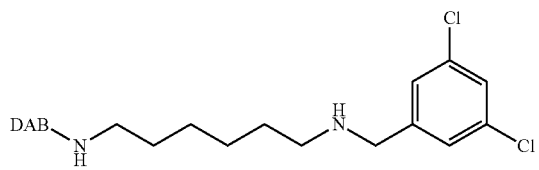

Deoxyactagardine B [6-(3',5'-dichlorobenzylamino)-hexylamine]monocarboxamide was prepared from deoxyactagardine B and 6-(3',5'-dichlorobenzylamino)-hexylamine utilising the procedure described for compound 1. Yield 51% Calculated for $[M+2H]^{+2}$ 1065.0, found 1065.8.

Compound 31

Deoxyactagardine B [8-(3',5'-dichlorobenzylamino)octylamine]monocarboxamide

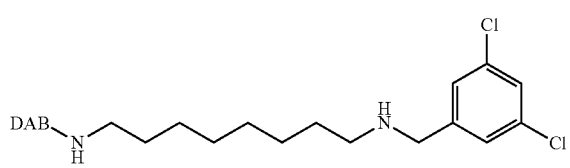

Deoxyactagardine B [8-(3',5'-dichlorobenzylamino)-octylamine]monocarboxamide was prepared from deoxyactagardine B and 8-(3',5'-dichlorobenzylamino)-octylamine utilising the procedure described for compound 1. Yield 36%. Calculated for $[M+2H]^{+2}$ 1058.0, found 1059.0.

Compound 32

Deoxyactagardine B [3-(2'-aminomethyl-4'-(2",4"-dichlorophenyl)-furanyl)propylamine]monocarboxamide

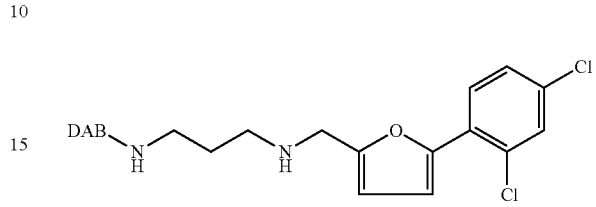

Deoxyactagardine B [3-(2'-aminomethyl-4'-(2",4"-dichlorophenyl)-furanyl)propylamine]monocarboxamide was prepared from deoxyactagardine B and 3-(2'-aminomethyl-4'-(2",4"-dichlorophenyl)-furanyl)propylamine utilising the procedure described for compound 1.
Yield 11%. Calculated for $[M+21-1]^{+2}$ 1077, found 1079.

Compound 33

Deoxyactagardine B [3-(2'-aminomethyl-4'-(2"-nitro-4"-chlorophenyl)-furanyl)propylamine]monocarboxamide

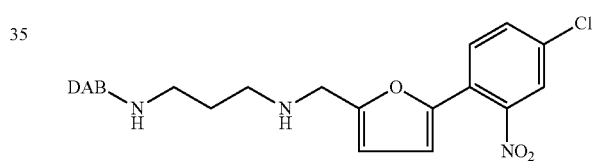

Deoxyactagardine B [3-(2'-aminomethyl-4'-(2"-nitro-4"-chlorophenyl)-furanyl)propylamine]monocarboxamide was prepared from deoxyactagardine B and [3-(2'-aminomethyl-4'-(2"-nitro-4"-phenyl)-furanyl)propylamine utilising the procedure described for compound 1.
Yield 11%. Calculated for $[M+2H]^{+2}$ 1084, found 1083.5.

Example 1

Compound 1 After Column Chromatography was Treated with 1.2 Eq of N-Methyl-D-Glucamine in 50% aqueous methanol. Evaporation of the resultant solution afforded the product as a white solid.

Alternative Method of Preparing a Salt of Example 1

Compound 1 (500 mg) was suspended in t-butanol (250 mL) and the suspension was left to stir at 45° C. for 4 hours until all solid dissolved. A solution of N-methyl glucamine (1M aq, 492 μL) was added and the mixture was stirred for a further 1 hour. The reaction mixture was flash frozen at −80° C. and then the material was freeze dried overnight, to afford Example 1 as a white solid (587 mg).

Example 2

10 mg/ml Formulation of the Salt of Example 1 as Final Formulation

Example 1 meglumine salt (10 mg) was dissolved in 1 mL of 5% glucose containing 1 mM potassium phosphate pH 5.0. The final pH of the solution was 8.40.

Example 3

10 mg/ml Formulation of the Salt of Example 1 as a Final Formulation

Example 1 (10 mg) was dissolved in 1 mL of 5% glucose containing 1.5 mM potassium phosphate pH 5.0. The final pH of the solution was 8.10.

Example 4

Formulation of the Salt of Example 1 as a Final Formulation

Example 1 meglumine salt (30 mg) was dissolved in 2.5 mL of 5% sorbitol. To the solution 100 mM HCl was added until the pH was 8.4. The final volume was then made to 3 mL with 5% sorbitol to afford a 10 mg/ml formulation in isotonic sorbitol.

Example 5

Formulation of the Salt of Example 1 as Liquid Concentrate

A 50 mg/mL formulation was prepared by dissolving 25 mg Example 1 as the meglumine salt in 500 μL of 5% mannitol. The pH of the solution was then adjusted to pH 8.4 by adding 25 μL of 100 mM HCl.

Example 6

Compound 1 (17 g) was charged to flask to which 9:1 t-BuOH:water (170 mL, 10 vol.) was added under nitrogen. The mixture was warmed to 28-29° C. and stirred at this temperature for 3 h after which time dissolution was observed. To this was added a solution of meglumine (3.14 g, 2 equiv, corrected for the water content of compound 1) dissolved in water (8.2 mL, 0.5 vol.) followed by a line rinse of 9:1 t-BuOH:water (8.5 mL, 0.5 vol.). The solution was stirred at 28-29° C. for 15 minutes and then filtered through GF filter paper. This was followed by a line rinse of 9:1 t-BuOH:water (2×17 mL, 2×1 vol.). The filtrates were combined and concentrated in vacuo at 25-28° C. to give a dry foam (23.9 g). Of this 23.1 g was transferred to a drying tray and dried in an oven that contained an open flask of water at 40° C. to reduce t-BuOH content.

Example 7

Compound 1 Meglumine Salt Prepared using a Method Similar to that Described in Example 5 (43 mg) was dissolved in 25% sorbitol solution (872 μL) to afford a pale yellow solution at a compound 1 concentration of 50 mg/mL. The pH of this solution was measured to be 8.90. Sequential aliquots of 100 mM HCl were then added until a pH of 8.30 was attained (total of 40 μL 100 mM HCl added). This sample was then frozen at −80° C. and then lyophilised overnight (using a ChemLab freeze drier attached to an Edwards R5 vacuum pump at less than 0.25 mBar) to afford a white solid.

The solid may be reconstituted by adding of water for injections (872 μL). Solid dissolved fully after gently shaking for less than 10 minutes to afford a clear, hypertonic solution at pH 8.4. This hypertonic 50 mg/mL concentrate can then diluted to a 10 mg/mL solution of compound 1 meglumine salt by addition of 200 μL of sample to 800 μL of water for injections to afford an isotonic solution at pH 8.10.

In Vivo Efficacy of Compounds in a Mouse Bacteraemia Model

Groups of 6 male CD-1 (Crl.) derived mice weighing 24±2 g were used. Mice were inoculated intraperitoneally (IP) with an $LD_{90-100}$ of Staphylococcus aureus methicillin resistant ATCC 33591 ($1.1 \times 10^7$ CFU/mouse) in 0.5 mL of BHI broth containing 5% mucin. Example 1 and vancomycin were dissolved in 15% HPbetaCD/4.4% glucose/0.5 mM $KH_2PO_4$, pH 5.0 and doses of 1, 3, 5, 10 and 20 mg/Kg were administered subcutaneously (SC) to test animals at 0, 2 and 24 hour(s) after bacteria challenge. The dosing volume was 5 mL/Kg. Mortality was recorded once daily for 7 days. The $ED_{50}$ for each compound was determined by nonlinear regression.

It was demonstrated that Example 1 at 3, 5, 10 and 20 mg/Kg×3, SC was associated with a significant antimicrobial effect against S. aureus (MRSA) in mice (at least 50% increase in survival rate) with an estimated $ED_{50}$ value of 1.07 mg/Kg).

Concurrently, vancomycin at 3, 5, 10 and 20 mg/Kg×3, SC exhibited significant antimicrobial effect against S. aureus (MRSA) in mice with an estimated $ED_{50}$ value of 3.0 mg/Kg. Mice which received Example 1 at 3 mg/Kg had a 100% survival rate.

In a second experiment Groups of 6 male CD-1 (Crl.) derived mice weighing 24±2 g were used. Mice were inoculated intraperitoneally (IP) with an $LD_{90-100}$ of Staphylococcus aureus methicillin resistant ATCC 33591 ($1.35 \times 10^8$ CFU/mouse) in 0.5 mL of BHI broth containing 5% mucin. Example 1 was dissolved in 5% dextrose/1.5 mM potassium phosphate, pH 5.0 and doses of 1, 3, 5 and 10 mg/Kg were administered intravenously (IV) to test animals at 1 and 13 hour(s) after bacteria challenge. The dosing volume was 5 mL/Kg. Mortality was recorded once daily for 7 days.

It was demonstrated that both vancomycin and Example 1 showed a dose-dependent increase in survival of mice after 7 days. For vancomycin the number of deaths at 0, 1, 3, 5 and 10 mg/kg was 5, 5, 3, 1 and 0 whereas for Example 1 the number of deaths was 5, 5, 4, 1 and 1 at these same doses.

Efficacy of Compounds in a Neutropaenic Mouse Thigh Infection Model.

In vivo efficacy of compounds of the present invention in the treatment of bacterial tissue infections was evaluated using a neutropaenic mouse thigh model.

Groups of 6 male ICR mice weighing 24±2 g were used. Test animals were immuno-suppressed by 2 intraperitoneal injections of cyclophosphamide, the first at 150 mg/Kg 4 days before infection (day−4) and the second at 100 mg/Kg 1 day before infection (day−1). On day 0, individual animals were inoculated intramuscularly (IM) into the right thigh of test animals with $1.15 \times 10^5$ CFU/mouse of Methicillin Resistant Staphylococcus aureus (MRSA, ATCC 33591) suspended in 100 μL of sterile PBS, pH 7.4. Vehicle and test substances were administered intravenously (IV) at a dose volume of 6 mL/Kg, 2 and 14 hours after thigh infection. Example 1 and vancomycin were dissolved in 15% hydroxypropyl-beta-cyclodextrin/4.4% glucose/1.5 mM potassium phosphate buffer, pH 7.0 and administered at doses of 5, 10, 20, 30 and 40 mg/Kg. At 26 hours after inoculation, muscle of the right thigh of each test mouse was harvested. From an additional group with no treatment, muscle of the right thigh was harvested at 2 hours after inoculation for the basal CFU determination. The removed muscle tissues were then homogenized in 3-4 mL of PBS, pH 7.4 with a ceramic mortar.

Homogenates of 0.1 mL were used for serial 10-fold dilutions and plated on Mueller Hinton broth in 1.5% Bacto agar for CFU determination.

Figure 2:
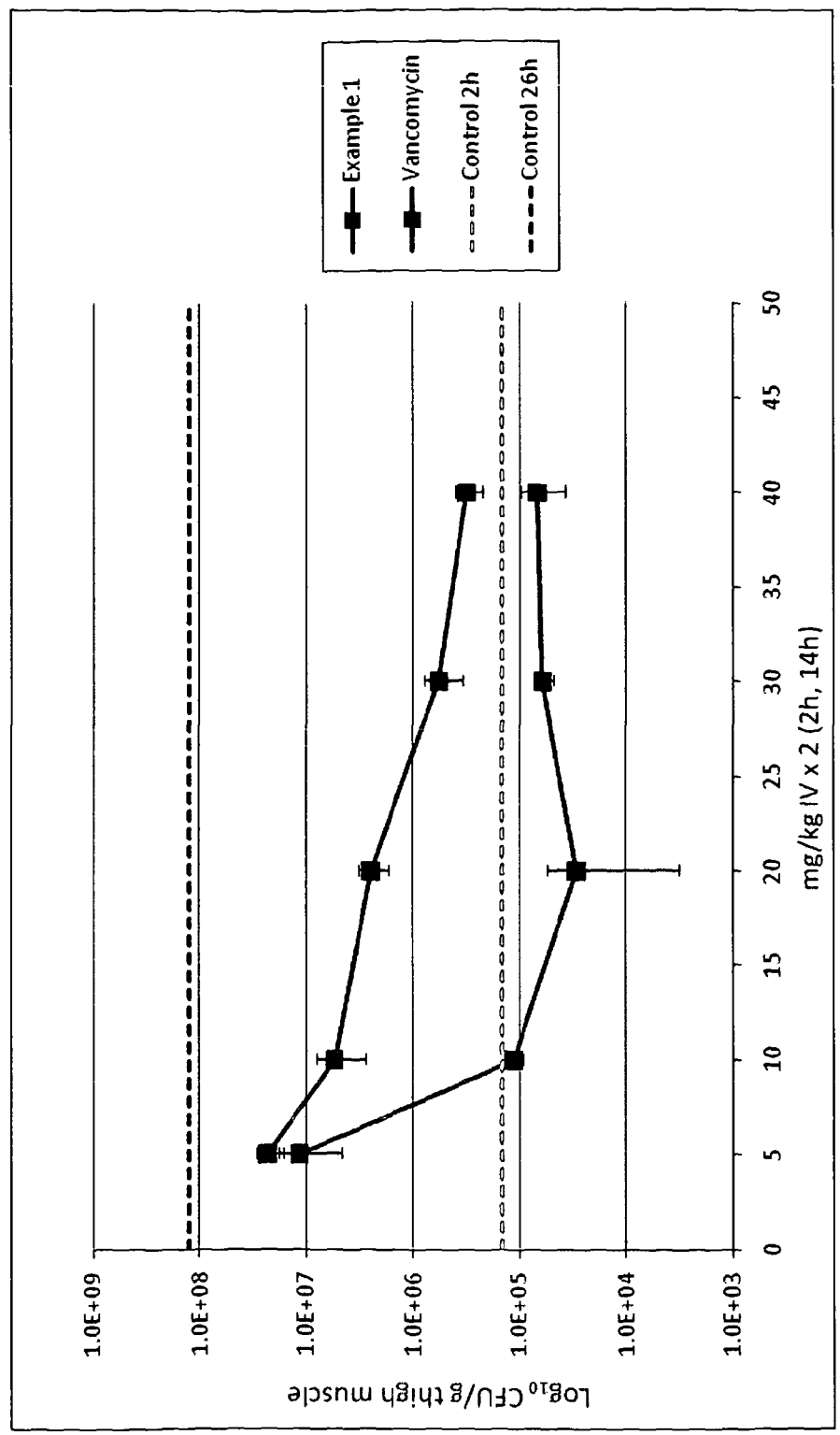

It was demonstrated that Example 1 dosed IV at 5, 10, 20 30 and 40 mg/Kg×2, was associated with a significant antimicrobial effect, resulting in a >1.000-fold reduction in CFU/g at 10 mg/kg and above. Concurrently, vancomycin also exhibited a significant antimicrobial effect with reductions of CFU/g of >100 fold at 30 mg/kg and above, whilst not attaining the >1,000-fold reduction observed for Example 1. Results (mean cfu/g) are graphically represented in FIG. 2.

In a further experiment groups of 6 male ICR mice weighing 24±2 g were used. Test animals were immunosuppressed by 2 intraperitoneal injections of cyclophosphamide, the first at 150 mg/Kg 4 days before infection (day-4) and the second at 100 mg/Kg 1 day before infection (day-1). On day 0, individual animals were inoculated intramuscularly (IM) into the right thigh of test animals with 1.5×10⁵ CFU/mouse of Methicillin Resistant *Staphylococcus aureus* (MRSA, ATCC 33591) suspended in 100 µL of sterile PBS, pH 7.4. Vehicle and test substances were administered intravenously (IV) at a dose volume of 8 mL/Kg, 2 and 14 hours after thigh infection. Example 1 was dissolved in 5% dextrose/1 mM potassium phosphate, pH 5.0 and administered at doses of 2.5, 5, 10, 15, 25 and 50 mg/Kg. At 26 hours after inoculation, muscle of the right thigh of each test mouse was harvested. From an additional group with no treatment, muscle of the right thigh was harvested at 2 hours after inoculation for the basal CFU determination. The removed muscle tissues were then homogenized in 3-4 mL of PBS, pH 7.4 with a ceramic mortar. Homogenates of 0.1 mL were used for serial 10-fold dilutions and plated on Mueller Hinton broth in 1.5% Bacto agar for CFU determination.

Figure 3:
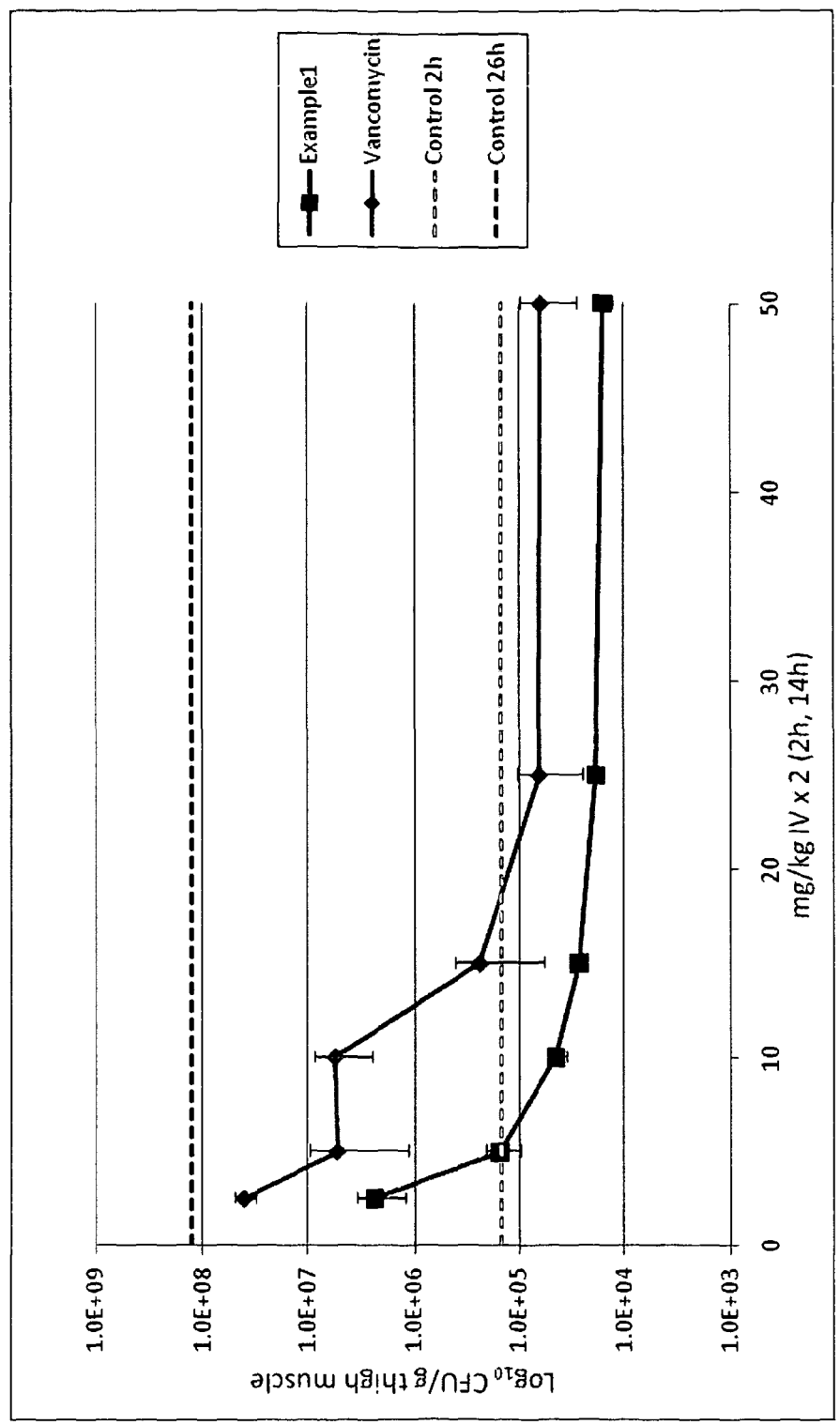

Both Example 1 and vancomycin showed a dose dependent reduction in the bacterial counts in the thigh tissue (FIG. 3).

In vivo Plasma Half-life of Compounds of the Present Invention in Mice.

The in vivo half-life of Compound 1 in mice was determined by measurement of its plasma concentrations at various time points following IV dosing. 18 male CD-1 mice aged 7-9 weeks were dosed IV with a 9.3 mL/Kg dose of a 3.2 mg/mL solution of Example 1 in 15% hydroxyl-propyl-beta-cyclodextrin/4.4% glucose/1 mM potassium phosphate (pH=7.6). Plasma samples were obtained at 10, 20, 30, 60, 120 and 240 min post-dose, sampling from 3 animals at each time point. Concentrations of Compound 1 in plasma were determined by LC-MS quantification.

Figure 4:
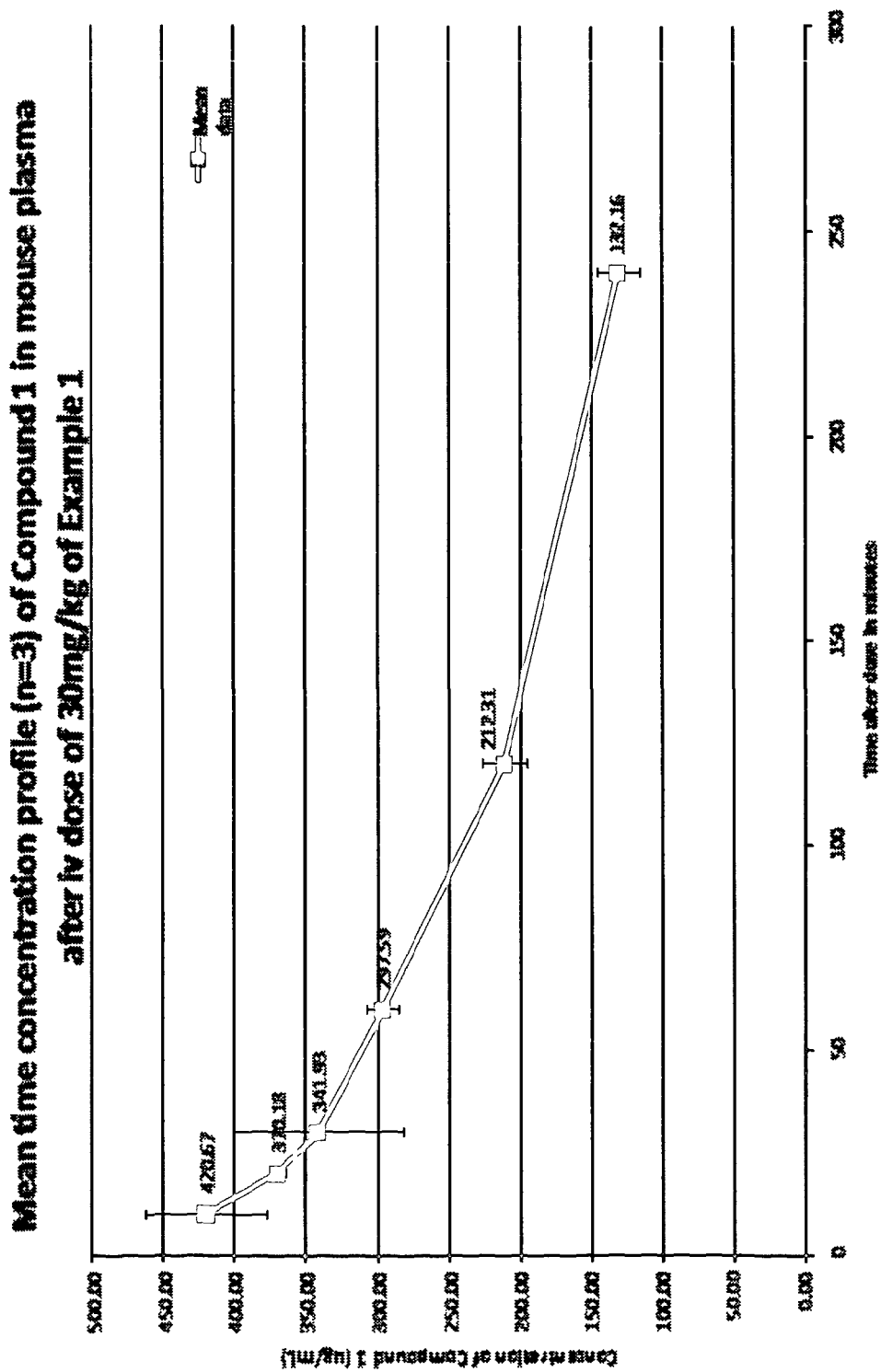
Figure 5:
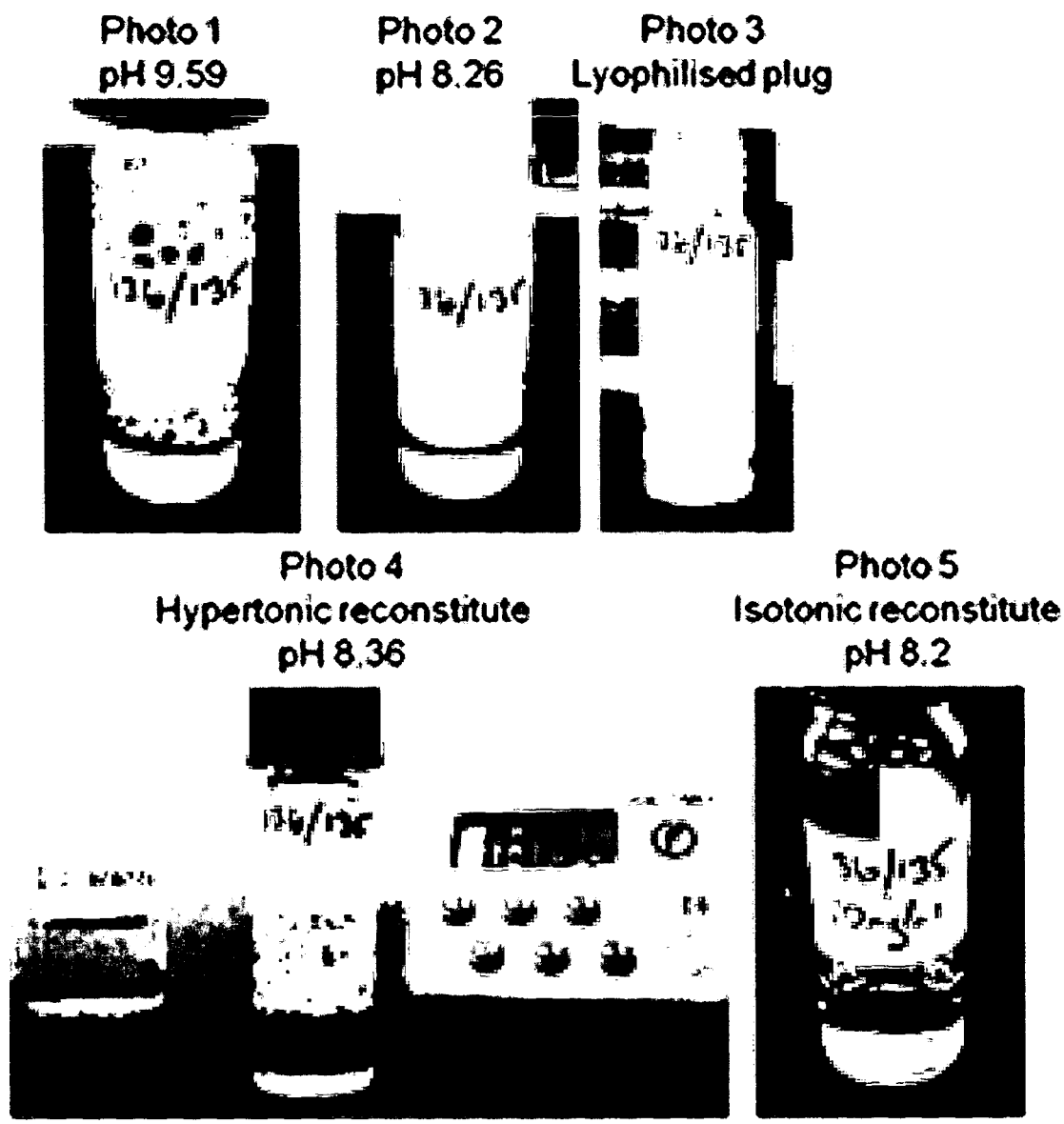
Figure 6:
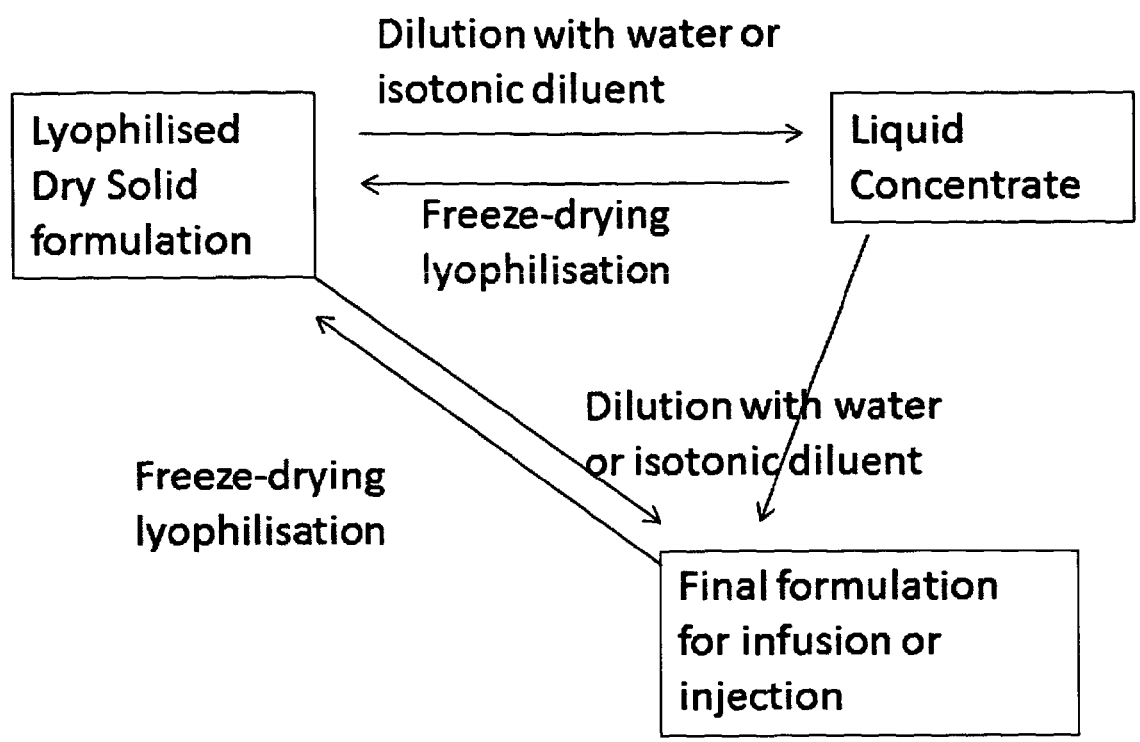

The data, summarised in FIG. 4, shows that Compound 1 has a plasma half-life of approximately 2 h in the mouse.

The invention claimed is:

1. A liquid pharmaceutical formulation of a type B lantibiotic comprising:
   a type B lantibiotic or a salt thereof,
   an isotonic aqueous solution comprising a sugar alcohol and/or a saccharide and optionally a buffer, where the sugar alcohol and/or the saccharide content in the formulation is in the range 1 to 10% w/w, and
   an inorganic salt selected from the group consisting of sodium chloride, potassium chloride and mixtures thereof, where the inorganic salt content is less than 0.5% w/v,
   wherein the formulation comprises a phase of particulates or sols having an average size of less than 500 nm and is clear of visual particulates.

2. The formulation according to claim 1 wherein the type B lantibiotic has a formula (III)

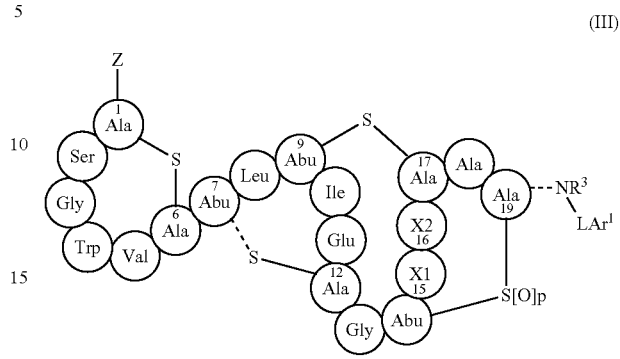

(III)

wherein:

X1 is an amino acid residue;

X2 is an amino acid residue;

R³ represents H or $C_{1-6}$ alkyl;

R⁴ represents H, $C_{1-6}$ alkyl, or —R⁴-L-Ar¹,

L represents a direct bond or is a straight or branched $C_{1-15}$ alkyl chain, wherein optionally one or more carbons are replaced by a heteroatom independently selected from N, O, or S, wherein the chain is optionally substituted by one or more oxo or nitro groups with the proviso that a heteroatom is not bonded directly to the N of the group —NR³R⁴;

Ar¹ represents phenyl substituted by one or two $NO_2$ groups or one to five halogen groups or one or two $C_{1-3}$ haloalkyl groups, or a combination thereof;

Z represents H, $C_{1-6}$ alkyl or an amino acid residue;

p represents 0 or 1; and the portion of III shown as:

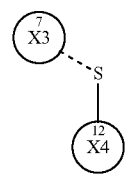

represents

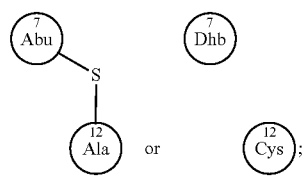

or a pharmaceutically acceptable salt thereof.

3. The formulation according to claim 2, wherein the type B lantibiotic of formula (III) has the structure:

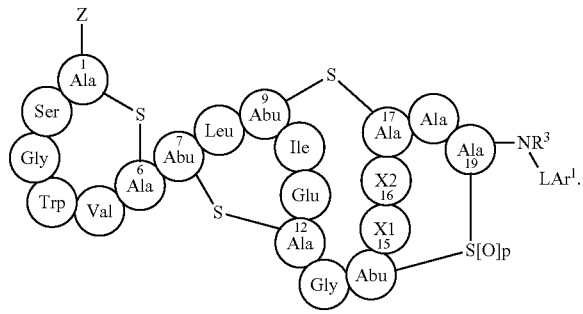

4. The formulation according to claim 2, wherein Z is H or Ala.

5. The formulation according to claim 4, wherein Z is H.

6. The formulation according to claim 2, wherein $Ar^1$ represents phenyl substituted by one or two $NO_2$ groups or one to five halogen groups, or a combination thereof.

7. The formulation according to claim 1, wherein the formulation or a concentrate thereof can be filtered through a 0.2 micron filter.

8. The formulation according to claim 1, wherein the formulation or a concentrate thereof is colloidal.

9. The formulation according to claim 1, where the formulation or a concentrate thereof generates a Tyndall beam when light is directed therethrough.

10. The formulation according to claim 1, wherein the formulation is administered by infusion.

11. The formulation according to claim 1, wherein the formulation is administered by direct injection.

12. The formulation according to claim 10, wherein the type B lantibiotic is present in a concentration of about 20 mg/mL.

13. The formulation according to claim 1, wherein the type B lantibiotic is deoxyactagardine B (3,5-dichlorobenzylamine) monocarboxamide.

14. The formulation according to claim 13, where the type B lantibiotic is in the form of the N-methyl glucamine salt.

15. The formulation according to claim 3, wherein X1 is Leu and X2 is Val, or X1 is Val and X2 is Ile.

16. The formulation according to claim 1 wherein the type B lantibiotic is monobasic.

17. The formulation according to claim 1 wherein the type B lantibiotic is deoxyactagardine B (3,5-dichlorobenzylamine) monocarboxamide, or a salt thereof.

18. A liquid concentrate of a formulation according to claim 1.

19. The liquid concentrate according to claim 18, wherein the type B lantibiotic is present at a concentration of about 50 mg/mL.

20. The liquid concentrate comprising a type B lantibiotic or a salt thereof, a buffer or HCl, for reconstitution into a formulation according to claim 1.

21. The liquid concentrate according to claim 20, wherein the type B lantibiotic is at a concentration of 30-60 mg/mL.

22. A lyophilised composition of a formulation according to claim 1.

23. A method of treating a bacterial infection in a patient in need thereof, comprising administering to the patient a therapeutically effective amount of a formulation according to claim 1.

24. The method of treating a patient according to claim 23, wherein the treatment is for infection by *Staphylococcus aureus*.

25. The method of treating a patient according to claim 24, wherein the *Staphylococcus aureus* is methicillin resistant.

* * * * *